United States Patent
Nishida et al.

(10) Patent No.: US 12,202,218 B2
(45) Date of Patent: Jan. 21, 2025

(54) METHOD FOR PRODUCING LENS TO BE FITTED TO EYE AND LENS TO BE FITTED TO EYE

(71) Applicant: OSAKA UNIVERSITY, Suita (JP)

(72) Inventors: Kohji Nishida, Osaka (JP); Koichi Baba, Osaka (JP); Shizuka Koh, Osaka (JP); Kei Ohkubo, Osaka (JP); Haruyasu Asahara, Osaka (JP); Tsuyoshi Inoue, Osaka (JP); Hiroshi Uyama, Osaka (JP); Taka-Aki Asoh, Osaka (JP)

(73) Assignee: Osaka University, Osaka (JP)

( * ) Notice: Subject to any disclaimer, the term of this patent is extended or adjusted under 35 U.S.C. 154(b) by 1069 days.

(21) Appl. No.: 17/254,120

(22) PCT Filed: Jun. 20, 2019

(86) PCT No.: PCT/JP2019/024601
§ 371 (c)(1),
(2) Date: Dec. 18, 2020

(87) PCT Pub. No.: WO2019/245002
PCT Pub. Date: Dec. 26, 2019

(65) Prior Publication Data
US 2021/0263339 A1    Aug. 26, 2021

(30) Foreign Application Priority Data

Jun. 20, 2018  (JP) .................................. 2018-117454

(51) Int. Cl.
*B29D 11/00* (2006.01)
*A61F 2/16* (2006.01)
*C08L 101/12* (2006.01)

(52) U.S. Cl.
CPC .......... *B29D 11/00038* (2013.01); *A61F 2/16* (2013.01); *C08L 101/12* (2013.01)

(58) Field of Classification Search
None
See application file for complete search history.

(56) References Cited

U.S. PATENT DOCUMENTS

| | | | |
|---|---|---|---|
| 3,873,696 A | 3/1975 | Randeri et al. | |
| 2010/0137982 A1 | 6/2010 | Culbertson et al. | |
| 2010/0208196 A1 | 8/2010 | Benrashid et al. | |
| 2014/0051812 A1 | 2/2014 | Burmaster | |
| 2018/0275426 A1 | 9/2018 | Jonin | |
| 2019/0217561 A1 | 7/2019 | Nakajima et al. | |
| 2019/0317337 A1 | 10/2019 | Sawada et al. | |
| 2020/0377453 A1 | 12/2020 | Takamori et al. | |

FOREIGN PATENT DOCUMENTS

| | | |
|---|---|---|
| CN | 108139608 | 6/2018 |
| JP | 48-085158 | 11/1973 |
| JP | 57-014821 | 1/1982 |
| JP | 07-504759 | 5/1995 |
| JP | 11-503183 | 3/1999 |
| JP | 2001-507255 | 6/2001 |
| JP | 2014-001159 | 1/2014 |
| JP | 2015-509114 | 3/2015 |
| JP | 6080281 B | 2/2017 |
| JP | 2017-155017 | 9/2017 |
| JP | 2017-227663 | 12/2017 |
| JP | 2018-047324 | 3/2018 |
| JP | 2018-054970 | 4/2018 |
| WO | 93/16736 | 9/1993 |
| WO | 96/31547 | 10/1996 |
| WO | 98/28026 | 7/1998 |
| WO | 2013/115917 | 8/2013 |
| WO | 2016/158707 | 10/2016 |

OTHER PUBLICATIONS

Office Action issued in corresponding Chinese Patent Application No. 201980041479.4 dated Jan. 26, 2022, 16 pages w/translation.
Ratner et al., "Biomaterials Science An Introduction to Materials in Medicine", 3rd Edition, Elsevier Inc. (2013), 3 pages.
Ohkubo et al., "Light-Driven C—H Oxygenation of Methane into Methanol and Formic Acid by Molecular Oxygen Using a Perfluorinated Solvent", Angew. Chem., Int. Ed., vol. 57, pp. 2126-2129 (2018).
International Search Report issued in International Application No. PCT/JP2019/024601, Sep. 17, 2019, 8 pages with translation.

*Primary Examiner* — Robert T Butcher
(74) *Attorney, Agent, or Firm* — HSML P.C.

(57) ABSTRACT

The present invention provides a new method for producing a lens to be fitted to an eye in a simple manner at a low cost. In order to achieve the aforementioned object, the present invention provides a method for producing a lens to be fitted to an eye, including the step of: hydrophilizing a surface of a polymer lens by reacting with a compound radical, wherein the compound radical is a radical containing one element selected from the group consisting of Group 15 elements and Group 16 elements, and a Group 17 element.

5 Claims, 9 Drawing Sheets

Before Irradiation

After Irradiation

METHOD FOR PRODUCING LENS TO BE FITTED TO EYE AND LENS TO BE FITTED TO EYE

TECHNICAL FIELD

The present invention relates to a method for producing a lens to be fitted to an eye and a lens to be fitted to an eye.

BACKGROUND ART

In the field of ophthalmology, as a lens to be fitted to an eye, for example, there are a lens to be fitted to an ocular surface (hereinafter, also referred to as an ocular surface lens), a lens to be fitted intraocularly (hereinafter, an intraocular lens), and the like. The ocular surface lens is a contact lens which is detachable (hereinafter, a detachable contact lens), and examples thereof include a hard contact lens (HCL) and a soft contact lens (SCL). In recent years, silicone hydrogel has become mainstream as a material of soft contact lenses (Patent Literatures 1 and 2, etc.). Examples of the intraocular lens include an artificial crystalline lens (Patent Literature 3, etc.) to be inserted into the eye to replace a crystalline lens whose function is lowered by cataract or the like, and an intraocular contact lens to be inserted into eye without removing a crystalline lens.

CITATION LIST

Patent Literatures

Patent Literature 1: JP 2018-054970 A
Patent Literature 2: JP 2017-227663 A
Patent Literature 3: JP 2018-047324 A

SUMMARY OF INVENTION

Technical Problem

The material of the detachable contact lens needs to have an oxygen permeability. Generally, a material having a high moisture content has high oxygen permeability, but on the other hand, there is a problem that such a material is liable to take away moisture on the ocular surface and thus the eye is liable to be dried. In this regard, the silicone hydrogel having a low moisture content has an advantage in that it is not liable to take away moisture on the ocular surface and thus the eye is not liable to be dried, and further the oxygen permeability is also high.

However, since the silicone hydrogel is hydrophobic, a hydrophilization treatment of the lens surface is necessary for use as a contact lens to be fitted to the ocular surface. As a method for hydrophilizing the polymer surface, for example, plasma treatment or the like is available, but there are problems such as complication of operation, treatment cost, and difficulty in reaction control.

Further, the inventors of the present invention have come to the idea that a higher utility can be obtained by imparting further functions to a lens to be fitted to an eye (lens to be fitted to an eye) including the detachable contact lens, the intraocular lens, and the like. Such an example has not yet existed.

With the foregoing in mind, it is an object of the present invention to provide a new method for producing a lens to be fitted to an eye in a simple manner at a low cost and a lens to be fitted to an eye which can be produced in a simple manner at a low cost.

Solution to Problem

In order to achieve the aforementioned object, the present invention provides a method for producing a lens to be fitted to an eye, including the step of: hydrophilizing a surface of a polymer lens by reacting with a compound radical, wherein the compound radical is a radical containing one element selected from the group consisting of Group 15 elements and Group 16 elements, and a Group 17 element.

The present invention also provides a first lens to be fitted to an eye formed of a polymer, wherein a surface of the polymer is an oxidized surface, and a variation X of a contact angle with water represented by the following equation (1) is larger than 0°:

$$X = A_0 - A \qquad (1)$$

$A_0$: a contact angle with water on a non-oxidized surface of the polymer $A$: a contact angle with water on an oxidized surface of the polymer $X$: a variation of the contact angle with water.

The present invention also provides a lens to be fitted to an eye formed of a polymer, wherein a surface of the polymer is hydrophilized, and an agent is carried on the surface of the polymer which has been hydrophilized.

Advantageous Effects of Invention

According to the present invention, a lens to be fitted to an eye can be produced in a simple manner at a low cost.

DESCRIPTION OF EMBODIMENTS

Figure 1:
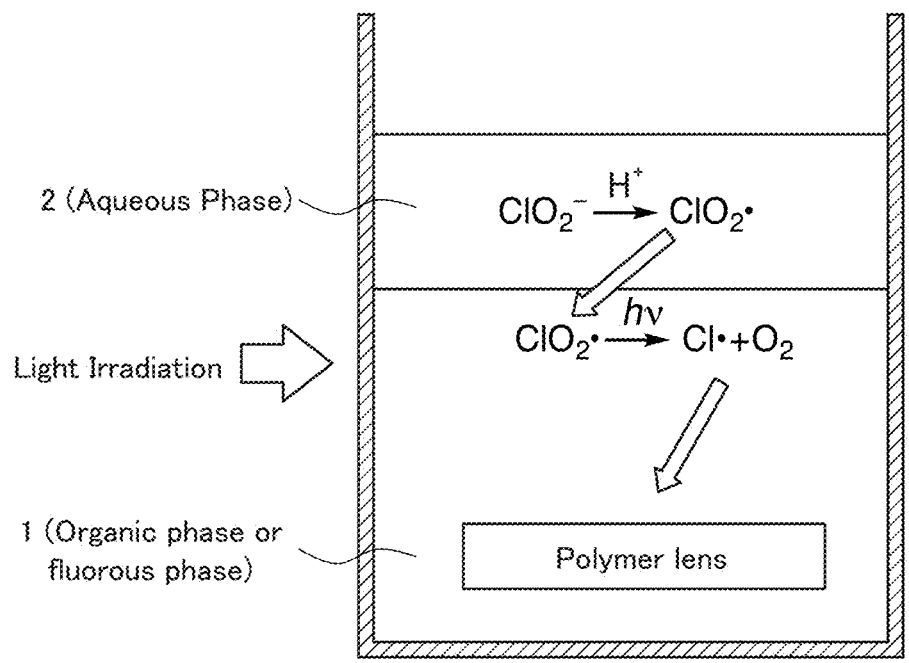
FIG. 1 is a diagram schematically showing an example of a hydrophilization treatment step in a method for producing a lens to be fitted to an eye of the present invention.

The present invention will be described below in more detail with reference to illustrative examples. The present invention, however, is not limited by the following description.

In the present invention, Group 15, Group 16, and Group 17 are groups of the periodic table.

In the present specification, "the lens to be fitted to an eye of the present invention" includes the first lens to be fitted to an eye and the second lens to be fitted to an eye, unless otherwise indicated. In the following description, the first lens to be fitted to an eye and the second lens to be fitted to an eye may be simply referred to as a "first lens to be fitted to an eye" and a "second lens to be fitted to an eye", respectively.

In the following description, the method for producing a lens to be fitted to an eye of the present invention may simply be referred to as a "production method of the present invention".

In the present invention, the "lens to be fitted to an eye" refers to a lens used by being fitted to an eye in general. In the present invention, "fitted" to eye includes, besides placement on an ocular surface, insertion into an eyeball and the like. The lens to be fitted to an eye is not particularly limited. The lens to be fitted to the ocular surface is also referred to as an ocular surface lens hereinafter, and is for example, a contact lens which can be detached and attached (detachable contact lens), and examples of the detachable contact lens include a hard contact lens, a soft contact lens, and a contact lens for use in orthokeratology. Further, examples of the lens to be fitted intraocularly (intraocular lens) include an intraocular contact lens to be inserted between the cornea and the crystalline lens without removing a crystalline lens and a lens (artificial crystalline lens) to be inserted into eye instead of the crystalline lens after removing a crystalline lens.

The production method of the present invention has the following effects in the production of the detachable contact lens, for example.

Regarding the detachable contact lens to be fitted to the ocular surface, in recent years, a soft contact lens (SCL) is generally made of silicone hydrogel as described above, which has an advantage that both high oxygen permeability and resistance to drying can be achieved. Then, a hydrophilization treatment of the surface of the contact lens is required as described above. As a hydrophilization treatment, as described above, a plasma treatment is known. Specifically, for example, a hydrophilization treatment is performed by activating the lens surface with plasma and then immersing it in a hydrophilic component. However, this method requires steps such as, for example, ultraviolet irradiation, heating, and addition of a polymerization assisting agent (initiator), which are very complicated. In addition, in this method, the hydrophilic layer (polar base layer) formed on the lens surface decreases with time, and the hydrophilicity of the surface may be degraded. In contrast, according to the present invention, by the hydrophilization treatment step using the compound radical, for example, it is possible to introduce a hydrophilic group into the lens surface in more simple manner at a low cost. Further, in the present invention, a group containing carbon of a polymer can be oxidized to be converted into a hydrophilic group such as a hydroxymethyl group ($-CH_2OH$), a formyl group ($-CHO$), and a carboxyl group ($-COOH$) by the hydrophilization treatment step, for example, as described below. Since these hydrophilic groups are fixed to the polymer surface by a covalent bond, for example, they are extremely unlikely to be decreased over time and are stable over a long period of time. Note that the above description is illustrative and does not limit the present invention. In the production method of the present invention, the material of the detachable contact lens is not limited to, for example, a silicone hydrogel, and various polymers as described below can be used.

Note that, in the present invention, the "silicone hydrogel" refers to a copolymer or a mixture of a hydrophilic gel and a silicone. The hydrophilic gel and the silicone may be bonded by a covalent bond, or may be bonded by another chemical bond such as an ionic bond, or may be simply mixed. The hydrophilic gel is not particularly limited, and is, for example, a gel of a hydrophilic polymer. The hydrophilic polymer is also not particularly limited, and examples thereof include polyvinylpyrrolidone, polyacrylamide, and derivatives thereof (e.g., polyacrylamide, polydimethylacrylamide), and polymers described in Table 1 described below, for example. Examples of the silicone hydrogel include the polymers described in Table 2 described below.

The production method of the present invention has following effects in the production of the intraocular lens, for example.

There is still no example of an intraocular lens carrying an agent. When an agent is carried on the intraocular lens, for example, after insertion into eye, an effect corresponding to the type of the agent can be obtained by sustained-release of the agent in the eye. More specifically, for example, by carrying a bactericide, an antibacterial agent, or the like as the agent on the intraocular lens, an infection after insertion into the eye can be prevented. On the other hand, for the agent to be carried on the intraocular lens in this manner, a hydrophilization treatment of the lens surface is necessary. One of the reasons for this is that, by chemically reacting a functional group such as a hydrophilic group introduced into the lens surface with a functional group of the agent to form a chemical bond or the like, an effect of carrying the agent on the lens surface can be obtained. Thus, both hydrophilic and hydrophobic agents can be carried. However, as described above, a hydrophilization treatment method using plasma treatment has problems such as complication of operation, treatment cost, and difficulty in reaction control as described above. In contrast, according to the present invention, by the hydrophilization treatment step using the compound radical, for example, it is possible to introduce a hydrophilic group into the lens surface in a simpler manner at a low cost. For this reason, as long as it is a lens after the hydrophilization treatment, for example, an agent can be carried on the lens surface through the hydrophilic group in a simpler manner at a low cost. Note that the above description is illustrative and does not limit the present invention. The effect of carrying the agent is not limited to, for example, the intraocular lens, and the same effect can be achieved, for example, in other lenses to be fitted to eyes such as the aforementioned detachable contact lens. In the present invention, the lens after the hydrophilization treatment step may or may not carry an agent, for example.

Since the surface of the polymer lens can be hydrophilized according to the production method of the present invention, in the present specification, a method for producing a lens to be fitted to an eye can be read as "a method for hydrophilizing a polymer lens" or "a method for hydrophilizing a lens to be fitted to an eye". In the present invention, according to the hydrophilization treatment step, the surface of the polymer lens can be altered. Therefore, in the present specification, the hydrophilization treatment step is also referred to as an "alteration treatment step". Further, when the polymer is oxidized by the hydrophilization treatment step, the hydrophilization treatment step is also referred to as an oxidation treatment step of the polymer.

For example, the upper limit value of the water contact angle of the lens to be fitted to an eye of the present invention may be 100° or less, 90° or less, less than 90°, 80° or less, 70° or less, 60° or less, 50° or less, 40° or less, 30° or less, 20° or less, or 10° or less, and the lower limit value is not particularly limited, and may be 0° or more, for example. The water contact angle can be measured, for example, as a contact angle (water droplet contact angle) when a water droplet is brought into contact with the lens to be fitted to an eye of the present invention. The smaller the water contact angle, the higher the hydrophilicity. From the viewpoint of conformability of the lens to the eye, it is preferable that the hydrophilic property is high. From the viewpoint of preventing adhesion of the lens to the eye (ease of removal from the eye), for example, it is preferable that the hydrophilicity is not too high. According to the present invention, for example, by appropriately controlling the conditions of the hydrophilization treatment step, it is also possible to control the hydrophilicity of the lens to be fitted to an eye.

In the present invention, a chain compound (e.g., an alkane, an unsaturated aliphatic hydrocarbon) or a chain substituent derived from a chain compound (e.g., a hydrocarbon group such as an alkyl group, an unsaturated aliphatic hydrocarbon group) may be, for example, linear or branched, the carbon number may be, for example, 1 to 40, 1 to 32, 1 to 24, 1 to 18, 1 to 12, 1 to 6, or 1 to 2, and in the case of an unsaturated hydrocarbon group, the carbon number may be, for example, 2 to 40, 2 to 32, 2 to 24, 2 to 18, 2 to 12, or 2 to 6. In the present invention, the number of ring members (the number of atoms constituting a ring) of a cyclic compound (e.g., a cyclic saturated hydrocarbon, a non-aromatic cyclic unsaturated hydrocarbon, an aromatic hydrocarbon, a heteroaromatic compound) or a cyclic group derived from a cyclic compound (e.g., a cyclic saturated hydrocarbon group, a non-aromatic cyclic unsaturated hydrocarbon group, an aryl group, a heteroaryl group) is not particularly limited, and may be, for example, 5 to 32, 5 to 24, 6 to 18, 6 to 12, or 6 to 10. When a substituent or the like has isomers, for example, the type of the isomer is not particularly limited, as a specific example, in the case of simply referring to a "naphthyl group" a 1-naphthyl group or a 2-naphthyl group may be used, for example.

In the present invention, the isomers are not particularly limited, and are, for example, tautomers or stereoisomers (e.g., a geometric isomer, a conformer, and an optical isomer). In the present invention, the salt is not particularly limited, and may be, for example, an acid addition salt or a base addition salt. An acid that forms the acid addition salt may be either an inorganic acid or an organic acid, and a base that forms the base addition salt may be either an inorganic base or an organic base. The inorganic acid is not particularly limited, and examples thereof include sulfuric acid, phosphoric acid, hydrofluoric acid, hydrochloric acid, hydrobromic acid, hydroiodic acid, hypofluorous acid, hypochlorous acid, hypobromous acid, hypoiodous acid, fluorous acid, chlorous acid, bromous acid, iodous acid, fluorine acid, chloric acid, bromic acid, iodic acid, perfluoric acid, perchloric acid, perbromic acid, and periodic acid. The organic acid also is not particularly limited, and examples thereof include p-toluenesulfonic acid, methanesulfonic acid, oxalic acid, p-bromobenzenesulfonic acid, carbonic acid, succinic acid, citric acid, benzoic acid, and acetic acid. The inorganic base is not particularly limited, and examples thereof include ammonium hydroxides, alkali metal hydroxides, alkaline-earth metal hydroxides, carbonates, and hydrogencarbonates. More specifically, the inorganic base may be, for example, sodium hydroxide, potassium hydroxide, potassium carbonate, sodium carbonate, sodium hydrogencarbonate, potassium hydrogencarbonate, calcium hydroxide, and calcium carbonate. The organic base also is not particularly limited, and examples thereof include ethanolamine, triethylamine, and tris(hydroxymethyl)aminomethane.

The present invention will be described below in more detail with reference to illustrative examples. The present invention, however, is not limited by the following description.

(1) Polymer Lens

In the method for producing a lens to be fitted to an eye of the present invention, as described above, in the hydrophilization treatment step, the surface of the polymer lens is hydrophilized by reacting with a compound radical. The polymer lens is a lens formed of a polymer as a raw material. The polymer lens is, for example, a molded body obtained by molding the polymer into the shape of lens. The type of the polymer is not particularly limited, and can be appropriately determined depending on, for example, the type of lens. The polymer may be, for example, one type or a mixture of two or more types. The polymer may be, for example, a polymer alloy or a polymer compound.

Examples of the polymer include a polymer having a melting point of room temperature or higher and a polymer having a glass transition temperature of room temperature or higher. Further, the polymer may be, for example, a polymer having a relatively high degree of crystallinity. In the case of a polymer having the melting point of the aforementioned condition, the crystallinity thereof is, for example, 20% or more, 30% or more, or 35% or more. The method for forming the polymer lens is not particularly limited, and may be, for example, a known molding method in which the polymer is melted by heating, then the shape is adjusted, and cooled.

The lens to be fitted to an eye to be produced in the present invention is a lens to be fitted to an eye in general as described above. In the present invention, the polymer which is a material for forming the lens to be fitted to an eye can be appropriately determined according to the type of the lens to be fitted to an eye, as described above. The polymer is not particularly limited and may be, for example, the same as a polymer which is a material for forming a general lens to be fitted to an eye. When the lens to be fitted to an eye of the present invention is the ocular surface lens such as the detachable contact lens, examples of the polymer include silicone hydrogel and the like, and any one type of them may be used alone, or two or more types of them may be used in combination. Examples of the silicone hydrogel include a polydimethylsiloxane gel (PDMS gel) and the like, and any one type of them may be used alone, or two or more types of them may be used in combination. When the lens to be fitted to an eye of the present invention is the intraocular lens, examples of the polymer include an acrylic resin and a silicone hydrogel, and any one type of them may be used alone, or two or more types of them may be used in combination. Examples of the acrylic resin include polymethyl methacrylate (PMMA) and the like, and any one type of them may be used alone, or two or more types of them may be used in combination.

As a specific example, the polymer may be, for example, a polymer described in Biomaterials Science An Introduction to Materials in Medicine (third edition), author: Buddy D. Ratner, Allan S. Hoffman, Frederick J. Schoen and Jack E. Lemons, publisher: Elsevier Inc (2013), and the like. When the lens is a soft hydrogel contact lens, for example, examples of the polymer include those described in Table 1 below, when the lens is a silicone hydrogel lens, for example, examples of the polymer include those described in Table 2 below, and when the lens is a gas permeable hard lens, examples of the polymer include those described in Table 3 below. In Tables 1 to 3 below, the "US generic name of polymer" represents a generic name of a polymer in the United States, and the "primary monomer" represents a major component of a raw material monomer of the polymer. For example, one type of the polymers of Tables 1 to 3 may be used alone or two or more types of them may be used in combination. The polymer may be, for example, a polymer containing one type of the raw material monomers described in Tables 1 to 3 or a copolymer containing two or more types of them, and two or more types of the polymer or copolymer may be used in combination.

TABLE 1

Examples of soft hydrogel contact lens material

| US generic name of polymer | Primary monomer |
|---|---|
| Polymacon | 2-hydroxymethyl methacrylate (HEMA), ethylene glycol dimethacrylate (EGDMA) |
| Hilafilcon B | HEMA, 1-vinyl-2-pyrrolidine (VP), EGDMA, 2-vinyl ethyl methacrylate (VEMA) |
| Bufilcon A | HEMA, N-(1,1-dimethyl-3-oxobutyl) acrylamide, 2-ethyl-2-(hydroxymethyl)-1,3-propanediol trimethacrylate |
| Etafilcon A | HEMA, methacrylic acid (MAA), EGDMA |
| Ocufilcon D | HEMA, sodium methacrylate (Na-MA), 2-ethyl-2-(hydroxymethyl)-1,3-propanediol trimethacrylate |
| Vilfilcon A | Methyl methacrylate (MMA), HEMA, VP, EGDMA |

TABLE 2

Examples of silicone hydrogel lens material

| US generic name of polymer | Primary monomer |
|---|---|
| Batafilcon A | VP, tris-(trimethylsyloxysilyl) provir vinyl carbamate (TPVC), N-carboxyvinyl ester (NCVE), poly(didimethylsiloxy)di(cyrilbutanol) bis(vinyl carbamate) (PBVC) |
| Lotrafilcon A | N, N-dimethylacrylamide (DMA), methacryloxypropyl tris(trimethylsiloxy) silane (TRIS), siloxane monomer |
| Lotrafilcon B | DMA, TRIS, siloxane monomer |
| Galyfilcon A | Monofunctional polydimethylsiloxane (MPDMS), DMA, HEMA, EGDMA, siloxane macromer, PVP |
| Senofilcon A | MPDMS, DMA, HEMA, tetraethylene glycol dimethacrylate (TEGDMA), siloxane monomer, PVP |
| Narafilcon A | MPDMS, DMA, HEMA, TEGDMA, siloxane monomer, PVP |
| Comifilcon A | VP, N-methyl-N-vinyl acetamide (MVA), isobolmil methacrylate (IBM), 1,3,5-triallyl-1,3,5-triazine-2,4,6(1H, 3H, 5H)-trione (TAIC), bis(methacryloyloxyethyl iminocarboxyethyloxypropyl)-poly(dimethylsiloxane)-poly(trifluoropropylmethylsiloxane)-poly(methoxy-poly [ethylene glycol] propylmethylsiloxane) (M3U), methacryloyloxy ethyl iminocarboxyethyloxypropyl-poly(dimethylsiloxy)-butyldimethylsilane (FM0411M), 2-hydroxybutyl methacrylate (HOB) |

TABLE 2-continued

Examples of silicone hydrogel lens material

| US generic name of polymer | Primary monomer |
|---|---|
| Enfilcon A | VP, MVA, IBM, TAIC, M3U, FM0411M, HOB |
| Asmofilcon A | Siroxanyl methacrylate (SIMA), siroxanyl acrylate (SIA), DMA, pyrrolidone derivatives |

TABLE 3

Examples of gas permeable hard lens material

| US generic name of polymer | Polymer or primary monomer |
|---|---|
| PMMA | Polymethylmethacrylate |
| Siflufocon A | silicone |
| Itafocon A | TRIS, MMA, dimethyl itakonate, MAA, TEGDMA |
| Paflufocon C | TRIS, 2,2,2-trifluoroethyl methacrylate, MAA, MMA, VP, EGDMA |
| Optifocon A | Co-Siloxy-fluoromethacrylate |
| Paflufocon D | TRIS, 2,2,2-trifluoroethyl methacrylate, MAA, MMA, siloxy-based nitride macromer, EGDMA |
| Melafocon A | TRIS, 2,2,2-trifluoroethyl methacrylate, VP, MAA, EGDMA |
| Tisilfocon A | Co-Fluoro-siloxanylstyrene |

When the lens is an intraocular lens (IOL), the type thereof is not particularly limited, and examples thereof include a monofocal IOL, a monofocal foldable IOL, a Toric IOL, a Phakic IOL, an aspherical lens, a multifocal IOL, and a foldable dual optical IOL. The intraocular lens may be, for example, an intraocular contact lens or an artificial crystalline lens, as described above. The polymer which is a material for forming the lens is not particularly limited, and examples thereof include a PMMA, a polysiloxane, a hydrophobic acrylate copolymer, a hydrophilic acrylate copolymer, a PMMA blue core monofilament, a polyamide, a polyvinylidene fluoride (PVDF), a polymer of a photopolymerizable polysiloxane macromer, and a silicone hydrogel, and any one type of them may be used alone or two or more types of them may be used in combination. The polymer may or may not contain, for example, an additive. The additive is not particularly limited, and examples thereof include an ultraviolet absorber, a violet light absorber, a blue light absorber, a yellow dye for a blue light filter, and an orange light absorber, and any one type of them may be used alone, or two or more types of them may be used in combination.

Other examples of the polymer include: the polyolefin (e.g., polyethylene (PE) such as low-density polyethylene and high-density polyethylene, and polypropylene (PP)), polyvinyl chloride, polystyrene, polylactic acid, polyhydroxy butyric acid, a silicone polymer, a phenolic resin, an epoxy resin, a diallyl phthalate resin, polycarbonate (PC), polymethylmethacrylate (PMMA), polydimethylsiloxane (PDMS), polyarylate such as amorphous polyarylate, polyether sulfone, polyparaphenylene vinylene, polythiophene, polyfluorene, polyphenylene sulfide (PPS), polyparaphenylene (PPP), a composite (PEDOT/PSS) of poly(3,4-ethylenedioxythiophene) (PEDOT) and polystyrene sulfonic acid (PSS), polyaniline/polystyrene sulfonic acid, poly(3-hydroxy alkanoic acid), polyvinylidene chloride, a styrene copolymer (e.g., an acrylonitrile-butadiene-styrene copolymer (ABS), an acrylonitrile-styrene copolymer resin (AS), a styrene-butadiene copolymer), a methacrylic resin, polyimide, polyetherimide, poly(trans-1,4-isoprene), an urea resin, polyester (e.g., polyethylene terephthalate, polybutylene terephthalate, polycaprolactone), polyamide (e.g., nylon (trade name)), polyether ether ketone, a cyclic cycloolefin polymer, polyethylene oxide, polypropylene oxide, and polyacetal. The polyolefin may be, for example, a polymer of an olefin having 2 to 20 carbon atoms, and may be, for example, a copolymer.

The polymerized form of the polymer is not particularly limited, and may be, for example, a homopolymer or a copolymer. The copolymer is not particularly limited, and may be, for example, a random copolymer, an alternating copolymer, a block copolymer, or a graft copolymer. In the case of the copolymer, for example, two or more types of repeating units (monomers) are used. The polymer may be, for example, a linear polymer, a branched polymer, or a network polymer.

In the present invention, the hydrophilization treatment step may be performed, for example, in the liquid reaction system (liquid phase) or in the gas reaction system (gas phase). When the polymer lens has a property of being easily dissolved in a liquid medium, for example, the gas phase reaction system is preferred.

The method for molding the polymer lens using the polymer is not limited in any way, as described above. Examples of the molding method include known methods such as compression molding, transfer molding, extrusion molding, calendar molding, inflation molding, blow molding, vacuum molding, injection molding, and the like. The shape of the polymer lens is not particularly limited, and is, for example, a shape corresponding to the type of an intended lens to be fitted to an eye (e.g., the ocular surface lens, the intraocular contact lens, the artificial crystalline lens).

In the present invention, the hydrophilization treatment step for the polymer lens may be performed, for example, in the liquid reaction system (liquid phase) or in the gas reaction system (gas phase) as described below. When the polymer has a property of being easily dissolved in a liquid medium, for example, it is preferable to perform the hydrophilization treatment step in the gas phase reaction system.

(2) Compound Radical

In the present invention, the compound radical is contained in a reaction system of the hydrophilization treatment step. The compound radical may be contained in the reaction system by, for example, generating it in the reaction system, or the compound radical separately generated may be contained in the reaction system. The method for generating the compound radical is not particularly limited. Regarding the generation of the compound radical, specific examples will be described below.

As described above, the compound radical is a radical containing at least one of Group 15 elements and Group 16 elements, and a Group 17 element. In the present invention, for example, any one type of the compound radicals may be used alone, or two or more types of them may be used in combination. In the present invention, the compound radical can be appropriately selected depending on, for example, the type of the polymer to be altered, the reaction condition, and the like.

The Group 15 element is, for example, N or P, the Group 16 element is, for example, O, S, Se, or Te, and the Group 17 element is, for example, F, Cl, Br, or I. Among the Group 15 element and the Group 16 element, the Group 16 element is preferable. Among the Group 16 elements, oxygen and sulfur are preferable. Examples of the radical containing the Group 16 element and the Group 17 element include the oxide radicals of halogen such as a $F_2O \cdot$ (difluoric oxygen radical), an $F_2O_2 \cdot$ (difluoric dioxygen radical), a $ClO_2 \cdot$ (chlorine dioxide radical), a $BrO_2 \cdot$ (bromine dioxide radical), and an $I_2O_5 \cdot$ (iodine oxide (V) radical).

(3) Reaction System

The reaction system in the hydrophilization treatment step is a reaction system containing the polymer and the compound radical. The reaction system may be, for example, a gas reaction system or a liquid reaction system as described above. In the hydrophilization treatment step, the reaction system may or may not be irradiated with light, for example. In other words, even if the polymer is not irradiated with light, the polymer and the compound radical can be reacted. Since there is no need to irradiate the polymer with light, for example, effects such as improvement in safety and cost reduction can be achieved. For example, a compound radical may be generated by light irradiation in a radical generation reaction system separate from a reaction system in the hydrophilization treatment step, and light irradiation may not be performed in the reaction system in the hydrophilization treatment step. As described above, the method for generating the compound radical itself is not particularly limited, and light irradiation may or may not be performed.

(3A) Gas Reaction System

When the reaction system is a gas reaction system, for example, a polymer lens may be placed in the gas reaction system containing the compound radical and the reaction system may be irradiated with light. However, in the present invention, the hydrophilization treatment step is not limited thereto. For example, as long as the surface of the polymer lens can be reacted with the compound radical, the hydrophilization treatment step may be performed without light irradiation. The gas reaction system may contain the radical, for example, and examples of the type of the gas phase in the gas reaction system include air, nitrogen, rare gas, and oxygen.

In the present invention, for example, the compound radical may be introduced or generated in the gas reaction system prior to or in parallel to the hydrophilization treatment step. In the former case, for example, a gas containing the compound radical may be introduced into the gas phase. In the latter case, for example, as will be described below, the compound radical generated in the liquid phase radical generation reaction system may be introduced by transferring the compound radical to a gas phase.

As a specific example, when the compound radical is the chlorine dioxide radical, for example, the chlorine dioxide radical can be present in the gas phase by introducing a chlorine dioxide gas into the gas phase. The chlorine dioxide radical may be generated in the gas phase by an electrochemical method, for example.

(3B) Liquid Reaction System

When the reaction system is a liquid reaction system, the liquid reaction system contains an organic phase, for example. The liquid reaction system may be a one-phase reaction system containing only the organic phase, or a two-phase reaction system containing the organic phase and an aqueous phase, for example. For the one-phase reaction system containing only the organic phase, for example, as will be described below, an aqueous phase containing a compound radical generation source may be prepared separately to generate the compound radical in the aqueous phase, the organic phase may then be mixed with the aqueous phase to dissolve (extract), in the organic phase, the compound radical generated in the aqueous phase.

(3B-1) Organic Phase

The organic phase contains the polymer lens placed therein, as mentioned above, and is, for example, a phase of an organic solvent containing the compound radical and the polymer lens placed therein.

The organic solvent is not particularly limited. As the organic solvent, one type may be used alone, or two or more types may be used in combination, for example. In the present invention, examples of the organic solvent include a halogenated solvent and a fluorous solvent, as mentioned above. Note that, for example, when the organic solvent is a fluorous solvent, the organic phase may be referred to as a "fluorous phase". When the liquid reaction system is the two-phase reaction system, the organic solvent is, for example, preferably, a solvent capable of forming the two-phase system, i.e., a solvent which separates from the aqueous solvent, which will be described below, constituting the aqueous phase, or a solvent slightly soluble or insoluble in the aqueous solvent.

The "halogenated solvent" refers to a solvent in which all or most of hydrogen atoms of hydrocarbon have been substituted with halogen, for example. The halogenated solvent may be, for example, a solvent in which 50% or more, 60% or more, 70% or more, 80% or more, or 90% or more of hydrogen atoms of the hydrocarbon are substituted with halogen. The halogenated solvent is not particularly limited, and examples thereof include methylene chloride, chloroform, carbon tetrachloride, carbon tetrabromide, and a fluorous solvent, which will be described below.

The "fluorous solvent" is a kind of the halogenated solvent, and refers to a solvent in which all or most of hydrogen atoms of hydrocarbon are substituted with fluorine atoms, for example. The fluorous solvent may be, for example, a solvent in which 50% or more, 60% or more, 70% or more, 80% or more, or 90% or more of hydrogen atoms of hydrocarbon are substituted with fluorine atoms. In the present invention, the use of the fluorous solvent is advantageous in reducing or preventing side reactions due to the low reactivity of the fluorous solvent itself, for example. Examples of the side reactions include an oxidation of the solvent, a hydrogen abstraction reaction of the solvent with the radical, halogenation (e.g., chlorination), and a reaction of a radical derived from a raw material compound and the solvent (e.g., a reaction of an ethyl radical and the solvent, for the hydrocarbon group in the side chain or at the terminal of the polymer being an ethyl group). The fluorous solvent is suitable for forming the two-phase reaction system due to its low miscibility with water, for example.

Examples of the fluorous solvent include solvents represented by the following chemical formulae (F1) to (F6). Among them, the fluorous solvent is, for example, preferably $CF_3(CF_2)_4CF_3$ having the following chemical formula (F1) where n=4.

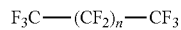

(F1)

n = 4, Boiling Point = 60° C.
n = 5, Boiling Point = 82° C.
n = 6, Boiling Point = 104° C.
n = 7, Boiling Point = 125° C.

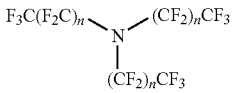

(F2)

n = 1 or 4
n = 1, Boiling Point = 135° C.

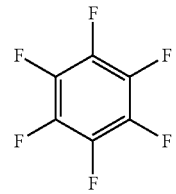

(F3)

Boiling Point = 81° C.

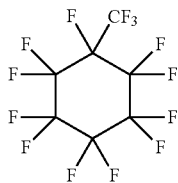

(F4)

Boiling Point = 76° C.

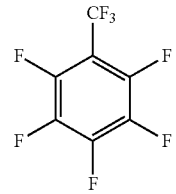

(F5)

Boiling Point = 104° C.

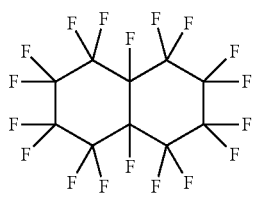

(F6)

Boiling Point = 142° C.

The boiling point of the organic solvent is not particularly limited. The organic solvent may be appropriately selected, for example, depending on the temperature conditions in the hydrophilization treatment step. For the high reaction temperature set in the hydrophilization treatment step, a high boiling point solvent may be selected as the organic solvent. Note that, for example, as will be described below, heating is not essential in the present invention, and the present invention can be implemented at ordinary temperature and normal pressure, for example. In such a case, the organic solvent need not be, for example, a high boiling point solvent, and a solvent having a not very high boiling point may be used from the viewpoint of ease of handling.

The organic phase may contain, for example, only the polymer lens, the compound radical, and the organic solvent, and may further contain other components. The other components are not particularly limited, and examples thereof include Brønsted acid, Lewis acid, and oxygen ($O_2$). In the organic phase, the other components may be, for example, in a state of being dissolved or undissolved in the organic solvent. In the latter case, the other components may be, for example, dispersed or precipitated in the organic solvent.

The organic phase contains the compound radical as mentioned above. The organic phase may contain the compound radical by generating the compound radical in a phase other than the organic phase and extracting the compound radical, for example. Specifically, for the reaction system being a one-phase reaction system containing only an organic phase, for example, the compound radical is generated separately in a phase other than the organic phase being the reaction system, the generated compound radical is extracted with the organic phase, and the organic phase containing the extracted compound radical as the reaction system can be used for the hydrophilization treatment step. The generation of the compound radical may be performed in the aqueous phase provided separately, as will be described below, for example. On the other hand, for the liquid reaction system being a two-phase system containing the organic phase and the aqueous phase, for example, the compound radical is generated in the aqueous phase, the generated compound radical is extracted from the aqueous phase in the organic phase, and an organic phase containing the aqueous phase and the compound radical can be used for the hydrophilization treatment step as the two-phase reaction system.

The polymer lens is placed in the organic phase. For example, from the viewpoint of efficiency of the reaction treatment to be described below, the polymer lens is preferably fixed in the organic phase such that a portion of the polymer lens to be subjected to a hydrophilization treatment is immersed in the organic phase and is not exposed from the organic phase.

(3B-2) Aqueous Phase

The aqueous phase is, for example, a phase of an aqueous solvent. Such aqueous solvent is, for example, a solvent which is separated from a solvent used in the organic phase. Examples of the aqueous solvent include water such as $H_2O$ and $D_2O$.

The aqueous phase may contain, for example, any components such as Lewis acid, Brønsted acid, and a radical generation source, as will be described below. The components in the aqueous phase may be, for example, in a state in which they are dissolved or undissolved in the aqueous solvent. In the latter case, the components may be, for example, in a state in which they are dispersed or precipitated in the aqueous solvent.

(4) Hydrophilization Step

In the present invention, the hydrophilization treatment step is a step of reacting the surface of the polymer lens with the compound radical as described above. In the hydrophilization treatment step, for example, the reaction system of the reaction may or may not be irradiated with light. Hereinafter, a method for irradiating the reaction system with light will be mainly described. The present invention, however, is not limited thereto. As described above, it is only necessary that the polymer surface can be reacted with the compound radical, and the hydrophilization treatment step may be performed without light irradiation. In that case, for example, the hydrophilization treatment step may be performed without light irradiation in the following description. As described above, since there is no need to irradiate the polymer lens with light, for example, effects such as improvement in safety and cost reduction can be achieved.

The reaction system contains the polymer lens placed therein, and the polymer lens may be altered. Specifically, the present invention allows the polymer lens to be altered easily in the presence of the compound radical. The present invention allows the degree of alteration of the polymer lens (e.g., the degree of modification such as oxidation) to be easily adjusted through adjustment of the amount of the compound radical, the light irradiation time, and the like, for example. This can prevent degradation of the polymer lens caused by excessive oxidation, and avoid deterioration of the characteristics that the polymer lens originally has, for example.

For the side chain of the polymer being a methyl group, in the hydrophilization treatment step, the methyl group ($-CH_3$) may be oxidized into at least one of, for example, a hydroxymethyl group ($-CH_2OH$), a formyl group ($-CHO$), or a carboxyl group ($-COOH$). This is assumed by the following mechanism. That is, the irradiation of the compound radical with light generates a radical of the halogen (e.g., a chlorine radical (Cl·)) and a molecule of the oxygen from the compound radical (e.g., a chlorine dioxide radical). Then, a methyl group of the polymer ($-CH_3$) is altered into a carboradical ($-CH_2·$) with a radical of the halogen (e.g., a chlorine radical (Cl·)) serving as a hydrogen-abstraction agent, and thereafter, the carboradical is altered into a hydroxymethyl group ($-CH_2OH$) with a molecule of the oxygen (e.g., $O_2$) serving as an oxidizing agent. Further, the hydroxymethyl group ($-CH_2OH$) is further oxidized into a formyl group ($-CHO$) or a carboxyl group ($-COOH$). The polymer being polypropylene (PP) allows oxidation in the following formula, for example.

Chemical Formula (1)

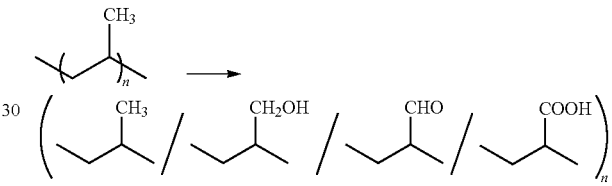

For the side chain of the polymer being an ethyl in the hydrophilization step, the ethyl group ($-CH_2CH_3$) is oxidized into, for example, a hydroxyethyl group ($-CH_2CH_2OH$), an acetaldehyde group ($-CH_2CHO$), or a carboxymethyl group ($-CH_2COOH$).

The polymer being polyethylene (PE) allows oxidation in the following formula, for example. Specifically, for example, a main chain carbon atom to which a hydrogen atom is bonded is oxidized to a hydroxymethylene group ($-CHOH-$), a carbonyl group ($-CO-$), or the like as in the following formula. Also, for example, for the polymer being polypropylene (PP), in addition to or as substitute for the oxidation, oxidation as in the following formula may occur.

Chemical Formula (2)

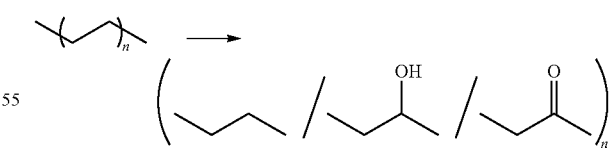

In the hydrophilization treatment step, the conditions of the light irradiation are not particularly limited. The wavelength of the irradiation light is not particularly limited, and the lower limit is, for example, 200 nm or more, and the upper limit is, for example, 800 nm or less. The light irradiation time is not particularly limited, and the lower limit is, for example, 1 second or more, and the upper limit is, for example, 1000 hours. The reaction temperature is not particularly limited, and the lower limit is, for example, −20°

C. or more, the upper limit is, for example, 100° C. or less or 40° C. or less, and is in the range from 0° C. to 100° C., or from 0° C. to 40° C. The atmospheric pressure during the reaction is not particularly limited, and the lower limit is, for example, 0.1 MPa or more, the upper limit is, for example, 100 MPa or less, 10 MPa or less, or 0.5 MPa or less, and is in the range from 0.1 to 100 MPa, from 0.1 to 10 MPa, or from 0.1 to 0.5 MPa. The reaction conditions during the hydrophilization treatment step are, for example, a temperature from 0° C. to 100° C. or from 0° C. to 40° C., and a pressure from 0.1 to 0.5 MPa. As described above, for example, the hydrophilization treatment step itself may be performed without light irradiation. The present invention allows the hydrophilization treatment step or all steps including the hydrophilization treatment step to be performed at normal temperature (room temperature) and normal pressure (atmospheric pressure) without heating, pressurizing, decompressing, and the like, for example. The "room temperature" is not particularly limited, and is from 5° C. to 35° C. For this reason, the present invention is applicable to the polymer having a low heat resistance, for example. Further, the present invention allows the hydrophilization treatment step or all steps including the hydrophilization treatment step to be performed in atmosphere without substitution with inert gas, for example.

The light source of the light irradiation is not particularly limited, and visible light included in natural light such as sunlight may be used. The natural light allows excitation to be performed in a simple manner, for example. Further, as the light source, for example, as a substitute for or in addition to the natural light, light sources such as a xenon lamp, a halogen lamp, a fluorescent lamp, a mercury lamp, and an LED lamp can be used. In the light irradiation, for example, a filter for cutting wavelengths other than the necessary wavelengths can further be used as appropriate.

As described above, the exposed surface of the polymer lens can be hydrophilized, and can be more effectively hydrophilized by light irradiation. For this reason, for example, by bringing the compound radical into contact with only a freely selected region of the polymer lens or irradiating only the freely selected region of the polymer lens with light in the presence of the compound radical, only the freely selected region of the polymer lens can be hydrophilized. In the former case, for example, a seal or the like is attached to the surface of the polymer lens excluding the freely selected region so that the compound radical does not come into contact with the surface excluding the freely selected region, and on the other hand, only the freely selected region is brought into contact with the compound radical, whereby only the freely selected region can be hydrophilized. In the latter case, for example, the surface of the compound radical excluding the freely selected region is masked, light irradiation to the masked region is blocked, and only the freely selected region is irradiated with light, whereby only the freely selected region can be hydrophilized. Thus, by selectively hydrophilizing only a freely selected region of the polymer lens, for example, it is possible to selectively carry the agent only in the freely selected region. Specifically, for example, in a contact lens, an agent can be selectively carried on a lens center portion corresponding to a cornea, or a lens peripheral portion corresponding to a conjunctiva, or the like.

When the reaction system is the liquid reaction system, for example, at least the organic phase may be irradiated with light in the hydrophilization treatment step. In the case of a one-phase reaction system consisting solely of the organic phase, for example, by irradiating the one-phase reaction system with light, the hydrophilization treatment step can be performed. In the case of a two-phase reaction system containing the organic phase and the aqueous phase, for example, only an organic phase may be irradiated with light, or the two-phase reaction system may be irradiated with light. In the case of the liquid reaction system, for example, the liquid reaction system may be irradiated with light while bringing the liquid reaction system into contact with air. In the case of the two-phase reaction system, light irradiation may be performed in a state in which oxygen is dissolved in the aqueous phase.

According to the present invention, in the hydrophilization treatment step, a radical of the Group 17 element (e.g., chlorine atom radical Cl·) and a molecule of the Group 15 element or the Group 16 element (e.g., oxygen molecule $O_2$) can be generated by a very simple method of simply irradiating with light in the presence of the compound radical, and the reaction (e.g., oxidizing reaction) with respect to the surface of the polymer lens can be performed to alter the surface of the polymer lens. Even under extremely mild conditions such as ordinary temperature and normal pressure, for example, the surface of the polymer lens can be efficiently altered by a simple method.

According to the present invention, for example, a lens to be fitted to an eye in which the polymer is altered can be obtained without using a toxic heavy metal catalyst or the like. Therefore, as described above, for example, the reaction can be performed under extremely mild conditions and the polymer can be efficiently altered by a method having a very small environmental load.

As a method of oxidizing a polymer, there is a method of adding a compound such as maleic acid or acrylic acid to a polymer such as PE or PP by using peroxide. However, since these compounds are accompanied by a cross-linking reaction, a decomposition reaction, and the like of PE and PP, the compounds are only introduced at about several weight %, and the introduction rate is low in practical use. In contrast, according to the present invention, the content of the site to be oxidized in the polymer can be relatively improved as compared to the conventional method.

Examples of the method of oxidizing the polymer include physical treatment methods such as corona discharge treatment, plasma discharge treatment, and grafting treatment. However, these methods involve problems of a complicated operation, treatment costs, and difficulty in reaction control. In contrast, according to the present invention, the surface of the polymer can be altered in a simple manner at a low cost.

(5) Compound Radical Generation Step

The invention may further include the step of generating the compound radical, for example. In the present invention, the compound radical generation step may be performed, for example, prior to or in parallel to the hydrophilization treatment step. The method for generating the compound radical is not particularly limited.

In the compound radical generation step, for example, the compound radical may be generated using a radical generation reaction system. The reaction system in the hydrophilization treatment step may be, for example, the gas reaction system (gas phase) or the liquid reaction system (liquid phase). The radical generation reaction system may be used as it is, after generating the compound radical, as the liquid reaction system in the hydrophilization treatment step, for example.

When the reaction system of the hydrophilization treatment step is the gas reaction system, for example, the radical generation reaction system may be prepared separately from the reaction system of the hydrophilization treatment step.

The radical generation reaction system may be, for example, an aqueous phase containing a compound radical generation source. The aqueous phase contains, for example, the compound radical generation source, and the compound radical is generated from the compound radical generation source in the compound radical generation step. The aqueous phase is, for example, a phase of an aqueous solvent, and the aqueous solvent is the same as described above. When the compound radical generated in the aqueous phase is hydrophobic, for example, the compound radical can be transferred to the organic phase by using a two-phase reaction system containing the organic phase and the aqueous phase as the radical generation reaction system. As described above, when the hydrophilization treatment step is performed in the gas reaction system, the reaction system for generating the compound radical may be, for example, only an aqueous phase or a two-phase reaction system of an aqueous phase and an organic phase. In the case where the compound radical is hydrophobic, for example, since the compound radical generated in the aqueous phase can be directly transferred to the gas phase, the radical generation reaction system may be only the aqueous phase.

When the reaction system of the hydrophilization treatment step is the liquid reaction system and contains the aqueous phase, for example, the aqueous phase may be the radical generation reaction system. The aqueous phase may be, for example, the same as the radical generation reaction system in the case where the reaction system of the hydrophilization treatment step is the gas reaction system. When the compound radical generated in the aqueous phase is hydrophobic, for example, a two-phase reaction system containing the organic phase and the aqueous phase can transfer the compound radical to the organic phase.

The compound radical generation source (radical generation source) is not particularly limited, and can be appropriately selected depending on, for example, the type of the compound radical. As the compound radical generation source, for example, only one type may be used alone, or two or more types may be used in combination. The source is, for example, a compound ion containing one element selected from the group consisting of Group 15 elements and Group 16 elements, and a Group 17 element. The compound ion is, for example, a halogen oxide ion. The halogen oxide ion is, for example, chlorite ion ($ClO_2^-$).

When the compound radical is a radical containing the Group 16 element and the Group 17 element, the compound radical may be, for example, an oxide radical of the halogen. In this case, the source may be, for example, a compound containing the Group 16 element and the Group 17 element corresponding to the compound radical. Specifically, the source may be, for example, halous acid ($HXO_2$) or salt thereof. The salt of the halous acid is not particularly limited, and may be, for example, metal salt. Examples of the metal salt include alkali metal salt, alkaline earth metal salt, and rare earth salt. When the compound radical is the chlorine dioxide radical, the source is not particularly limited, and may be, for example, chlorite ($HClO_2$) or salt thereof. Specifically, examples of the source include sodium chlorite ($NaClO_2$), lithium chlorite ($LiClO_2$), potassium chlorite ($KClO_2$), magnesium chlorite ($Mg(ClO_2)_2$), and calcium chlorite ($Ca(ClO_2)_2$). Among them, sodium chlorite ($NaClO_2$) is preferred from the viewpoint of cost and ease of handling. For example, the same method can be used for sources of other compound radicals. Specifically, examples of the sources of other compound radicals include bromate salt such as sodium bromite and iodite salt such as sodium bromite.

The concentration of the source in the aqueous phase is not particularly limited. When the source is the compound, in terms of the compound ion concentration, the lower limit of the concentration thereof is 0.0001 mol/l or more and the upper limit thereof is 1 mol/l or less, for example, and, in terms of the number of moles of the compound ion, the lower limit of the concentration thereof is $1/100000$ times or more of the number of moles of the raw material and the upper limit of the concentration thereof is 1000 times or less of the number of moles of the raw material, for example. When the source is halous acid or halite (e.g., chlorous acid or chlorite), in terms of a halite ion (e.g., chlorite ion ($ClO_2$)) concentration, the lower limit of the concentration thereof is 0.0001 mol/l or more and the upper limit of the concentration thereof is 1 mol/l or less, for example, and in terms of the number of moles of the halite ion (e.g., chlorite ion ($ClO_2$)), the lower limit of the concentration thereof is $1/100000$ times or more of the number of moles of the raw material and the upper limit of the concentration thereof is 1000 times or less of the number of moles of the raw material, for example. The above-described concentrations can be applied also to other sources, for example.

The aqueous phase may further contain, for example, at least one of a Lewis acid and a Brønsted acid, which may act on the source (radical generation source) to produce the compound radical. At least one of the Lewis acid and Brønsted acid is, for example, at least one of a Lewis acid and a Brønsted acid containing a Group 1 element. The Group 1 element is, for example, at least one selected from the group consisting of H, Li, Na, K, Rb, and Cs. The aqueous phase may contain, for example, only one or both of the Lewis acid and the Brønsted acid, or one substance may serve as both of the Lewis acid and the Brønsted acid. Only one type of the Lewis acid and the Brønsted acid may be used alone, or two or more types may be used in combination. In the present invention, the "Lewis acid" means, for example, a substance which serves as a Lewis acid with respect to the compound radical generation source.

In the aqueous phase, the concentration of at least one of the Lewis acid and the Brønsted acid is not particularly limited, and can be appropriately determined depending on, for example, the type of the polymer to be altered. The lower limit of the concentration is 0.0001 mol/l or more and the upper limit of the concentration is 1 mol/l or less, for example.

The Brønsted acid is not particularly limited, and may be, for example, an inorganic acid or an organic acid. Specific examples of the Brønsted acid include trifluoromethanesulfonic acid, trifluoroacetic acid, acetic acid, hydrofluoric acid, hydrochloric acid, hydrobromic acid, hydroiodic acid, sulfuric acid, sulfurous acid, nitric acid, nitrous acid, phosphoric acid, and phosphorous acid. The acid dissociation constant $pK_a$ of the Brønsted acid is, for example, 10 or less. The lower limit of the $pK_a$ is not particularly limited, and is, for example, −10 or more.

The aqueous phase contains, for example, the compound ion and a Brønsted acid, and is preferably, for example, an aqueous phase in which the compound and a Brønsted acid (e.g., hydrochloric acid) are dissolved in an aqueous solvent. As a specific example, when the compound radical is a chlorine dioxide radical, the aqueous phase preferably contains, for example, chlorite ion ($ClO_2$) and a Brønsted acid, and is preferably, for example, an aqueous phase in which the sodium chlorite ($NaClO_2$) and a Brønsted acid (e.g., hydrochloric acid) are dissolved in an aqueous solvent.

In the aqueous phase, for example, the Lewis acid, the Brønsted acid, the radical source, and the like may be dissolved or undissolved in the aqueous solvent. In the latter case, they may be dispersed or precipitated in the aqueous solvent, for example.

The compound radical generating step is not particularly limited, and for example, the compound radical (e.g., chlorine dioxide radical) can be naturally generated from the source (e.g., the compound ion, e.g., chlorite ion) by causing the aqueous solvent to contain the compound radical generation source. For example, it is preferable that the source be dissolved in the aqueous solvent in the aqueous phase, and it is preferable that the aqueous phase be left to stand still. In the compound radical generating step, the aqueous phase can further accelerate the generation of the compound radical by, for example, causing at least one of the Lewis acid and the Brønsted acid to coexist. In the compound radical generating step, the compound radical can be generated, for example, by irradiating the aqueous phase with light. It is to be noted that the compound radical can also be generated, for example, by simply allowing the aqueous phase to stand still without irradiating the aqueous phase with light. Since the compound radical generated from the source in the aqueous phase in the reaction system is poorly soluble in water, it is dissolved in the organic phase in the reaction system.

The mechanism by which the compound radical is generated from the compound ion in the aqueous phase is presumed, for example, as in FIG. 1 (in the case of a two-phase system of an organic phase and an aqueous phase in an aqueous phase reaction system) to be described below. Note that the above description is illustrative and does not limit the present invention.

When the reaction system is the liquid reaction system and is a two-phase reaction system containing the organic phase and the aqueous phase, after generating the compound radical as described above, the liquid reaction system may be directly subjected to the above-described hydrophilization treatment step. Since the compound radical generated from the source in the aqueous phase in the reaction system is poorly soluble in water, the compound radical is dissolved in the organic phase in the reaction system. For example, the hydrophilization treatment step of altering the polymer may be performed by further irradiating the liquid reaction system, in which the compound radical is generated, with light. In this case, for example, by irradiating the liquid reaction system with light, the compound radical generating step and the hydrophilization treatment step can be performed successively. In the present invention, for example, better reaction efficiency can be obtained by performing the compound radical generating step and the hydrophilization treatment step in the two-phase reaction system.

On the other hand, when the reaction system in the hydrophilization treatment step is the liquid reaction system and is a one-phase reaction system containing only the organic phase, for example, the compound radical may be generated in the aqueous phase by the above-described method and the generated compound radical may be dissolved (extracted) in the organic phase, and then the aqueous phase may be removed and the organic phase containing the compound radical may be subjected to the hydrophilization treatment step as the one-phase reaction system.

FIG. 1 schematically shows an example of the compound radical generating step and the hydrophilization treatment step using the two-phase reaction system. In FIG. 1, the chlorine dioxide radical as the compound radical is shown as a specific example, however, the present invention is not limited thereto in any way. As shown in FIG. 1, in the reaction system, two layers of an aqueous layer (the aqueous phase) and an organic layer (the organic phase) are separated from each other in a reaction container, and are in contact with each other only at an interface. The upper layer is an aqueous layer (the aqueous phase) 2, and the lower layer is an organic layer (the organic phase) 1. The organic phase 1 may be, for example, a fluorous phase. It is to be noted that, while FIG. 1 is a cross-sectional view, for viewability, hatching of the aqueous layer 2 and organic layer 1 is omitted. As shown in FIG. 1, chlorite ion ($ClO_2^-$) in the aqueous layer (aqueous phase) 2 reacts with an acid to generate a chlorine dioxide radical ($ClO_2\cdot$). Since the chlorine dioxide radical ($ClO_2\cdot$) is poorly soluble in water, it is dissolved in the organic phase 1. Subsequently, by irradiating the organic layer 1 containing the chlorine dioxide radical ($ClO_2\cdot$) with light to apply light energy to the organic layer, a chlorine dioxide radical ($ClO_2$) in the organic layer 1 is decomposed to generate a chlorine radical ($Cl\cdot$) and an oxygen molecule ($O_2$). As a result, the polymer lens in the organic layer (organic phase) 1 is oxidized and the surface is altered. FIG. 1 is merely an illustrative example and does not limit the present invention in any way.

While the aqueous layer 2 is the upper layer and the organic layer 1 is the lower layer in FIG. 1, for example, if the organic layer 1 has lower density (specific gravity) than the aqueous layer 2, the organic layer 1 serves as the upper layer. The polymer lens may be fixed in the reaction container such that the polymer lens is disposed in the upper organic layer. In this case, the site where the polymer lens is fixed may be provided in the reaction container or may be provided outside the reaction container, for example. In the latter case, for example, the polymer lens may be suspended from the outside and immersed in the organic layer.

While FIG. 1 shows the two-phase reaction system, in the production method of the present invention, the hydrophilization treatment step may be performed in a one-phase reaction system containing only an organic phase. In this case, for example, an aqueous phase containing the compound radical generation source is separately prepared, the compound radical is generated in the aqueous phase, and then the organic phase is mixed with the aqueous phase to dissolve (extract) the compound radical generated in the aqueous phase into the organic phase. Then, the aqueous phase and the organic phase are separated, the organic phase is recovered, and the polymer is placed, thereby obtaining a one-phase reaction system. The hydrophilization treatment step is performed by irradiating the one-phase reaction system alone with light in the presence of the compound radical.

(6) Functional Group Introducing Step

The method for producing a lens to be fitted to an eye of the present invention may further include the step of introducing a functional group into a changed site of the polymer forming the polymer lens, for example. The changed site (modified site) in the polymer may be, for example, a site into which an element such as described above has been introduced, and as a specific example, the changed site may be an oxidized site.

According to the method for producing a lens to be fitted to an eye of the present invention, as described above, the polymer forming the polymer lens can be modified by the hydrophilizing treatment step, and physical properties of the polymer can be further changed by introducing a functional group, as described above.

According to the method for producing a lens to be fitted to an eye of the present invention, for example, various functions can be imparted to the polymer by further introducing a functional group.

According to the method for producing a lens to be fitted to an eye of the present invention, for example, physical properties can be changed by introducing a functional group. Introducing a functional group may be, for example, applying an agent to the polymer lens. By changing physical properties of the polymer in this manner, for example, the applications of the polymer lens can be expanded to a delivery material, a sustained release material, and the like, for example.

(7) Agent Carrying Step

The method for producing a lens to be fitted to an eye of the present invention may further include the step of carrying an agent on the surface of the lens that has been subjected to the hydrophilization treatment step. In the step perspective view of (a) to (c) of FIG. 8, an example of the method for producing a lens to be fitted to an eye of the present invention including the agent carrying step is schematically shown. First, as shown in (a) of FIG. 8, a polymer lens 11 is provided. Next, the hydrophilization treatment step is performed as shown in (b) of FIG. 8 to alter the surface of the polymer lens 11, thereby obtaining an altered surface 12. Further, the agent carrying step is performed as shown in (c) of FIG. 8 to carry an agent 13 on the altered surface 12. Note that, in FIG. 8, the lens to be fitted to an eye to be produced is not particularly limited, and may be, for example, the ocular surface lens or the intraocular lens. Further, for example, other steps such as the step of introducing a functional group may or may not be performed after the hydrophilization treatment step and prior to the agent carrying step. In the step of introducing the functional group, for example, a hydrophilic functional group may be introduced. Introducing a hydrophilic functional group to the lens surface can also be referred to as hydrophilizing the lens surface.

In the present invention, for example, since the surface of the lens to be fitted to an eye is hydrophilized, it is easy to form an ionic bond, a hydrogen bond, a covalent bond (e.g., a peptide bond), or the like with an agent. Thus, it is easy to carry the agent on the surface of the lens to be fitted to an eye. For example, the agent may have an amino group and form a peptide bond with the surface of the lens to be fitted to an eye. Note that the above description is illustrative and does not limit the present invention.

The agent is not particularly limited, and may be, for example, the same as a general agent used in the eye or any other agent. Examples of the functions, applications, and the like of the agent include bactericides, antibacterial agents, antivirus agents, antiallergic agents, antifungal agents, anti-inflammatory agent, antibiotics, corticosteroids, corneal therapeutic agents, conjunctival therapeutic agents, Glaucoma corrective agents, mydriatics, cycloplegic, local anesthetic, anti-cataract agents, and vitamins. Examples of the substance name of the agent include cefotiam, cefmenoxime, cefotiam hydrochloride, cefmenoxime hydrochloride, ofloxacin, levofloxacin, acyclovir, iodine/polyvinyl alcohol, pimaricin, azulensulfonic acid sodium hydrate, lysozyme hydrochloride, glycyrrhizic acid dikalium, amlexanox, cromoglycate sodium, hydrocortisone acetate, prednisolone acetate, dexamethasone, fluorometholone, chondroitin sulfate ester sodium, boric acid/inorganic salt combination, flavin adenine dinucleotide sodium/chondroitin sulfate sodium, carteolol hydrochloride, cyclopentrate hydrochloride, phenilefurin hydrochloride, tropicamide, tropicamide/phenilefurin hydrochloride, oxybuprokine hydrochloride, pyrenoxin, glutathion, cyanocobalamine, flavin adenine dinucleotide sodium, glucose/inorganic salt combination, and purified hyaluron sodium hydrochloride. Further, the agent may be, for example, an isomer, a salt, a hydrate, or the like thereof. Note that, in the present invention, the isomer and salt of chemical substance are not particularly limited, and are, for example, those as described above. In addition, only one type of the agents may be used alone or two or more type of them may be used in combination. Specifically, for example, in one lens to be fitted to an eye, two or more different types of agents may be carried on different sites, and in this case, the lens to be fitted to an eye may be the ocular surface lens or the intraocular lens. For example, when the lens to be fitted to an eye is an ocular surface contact lens, a corneal therapeutic agent may be carried at a center portion of a lens and a conjunctival therapeutic agent may be carried at a peripheral portion of a lens, respectively.

The specific method of the agent carrying step is not particularly limited, and may be, for example, the same as or according to general methods of carrying an agent on a solid surface, or may be appropriately set conditions by referring to these methods. Methods of carrying an agent on a solid surface are described in, for example, WO2016/158707A1, JP 2014-001159 A, and the like. In the agent carrying step, for example, the agent or a solution thereof may be applied to the lens surface after the hydrophilization treatment step, or the lens that has been subjected to the hydrophilization treatment step may be immersed in the agent or a solution thereof. During the immersion, for example, the agent or a solution thereof may or may not undergo ultrasonic treatment, heating, pressure, pH adjustment, or the like. Further, after the application or immersion, the lens may or may not be subjected to washing, drying, or the like, if necessary. The temperature, time, and the like in application, immersion, drying, and the like are not particularly limited and can be appropriately set. In addition, in the agent carrying step, as described above, the lens surface and the agent may form an ionic bond, a hydrogen bond, or the like, or the lens surface and the agent may chemically react with each other to form a covalent bond.

In the present invention, by carrying an agent on the surface of the lens to be fitted to an eye, for example, the agent can be sustain-released from the lens to be fitted to an eye.

Further, in the present invention, by carrying an agent on the surface of the lens to be fitted to an eye, an effect corresponding to the type of the agent can be obtained. For example, since the intraocular lens is inserted into the eye, there is a possibility of infection or the like in some cases. Therefore, when an antibacterial agent, a bactericide, or the like is carried on the surface of the intraocular lens, an effect such as the prevention of the infection can be obtained.

(8) Lens to be Fitted to Eye

In the lens to be fitted to an eye of the present inventive, as described above, the variation X of the contact angle with water represented by $X=A_0-A$ is larger than 0°. As described above, $A_0$ is the contact angle with water on the non-oxidized surface of the polymer and A is the contact angle with water at the oxidized surface of the polymer. The variation X of the contact angle with water is, for example, 1° or more, 2° or more, 5° or more, 10° or more, 20° or more, or 30° or more, and the upper limit of the contact angle with water is $A_0$ or less, is not particularly limited, and is, for example, 60° or less. The method for measuring the contact angle with water and the measuring device for the contact angle are not particularly limited, and are, for example, as those described in the following examples.

The method for producing the lens to be fitted to an eye of the present invention is not particularly limited, and for example, the polymer lens can be produced by altering the polymer lens by the hydrophilization treatment step. The polymer lens to be treated is, for example, as described above.

In the lens to be fitted to an eye of the present invention, for example, the polymer be polypropylene, and in an infrared absorption spectrum of the oxidized surface, the ratio C=O/C—H>0 of an area of a peak derived from C—H expansion and contraction in 2800 to 3000 cm$^{-1}$ to an area of a peak derived from C=O expansion and contraction in 1700 to 1800 cm$^{-1}$ may be larger than 0. The ratio C=O/C—H>0 is, for example, 0.0001 or more, 0.001 or more, 0.02 or more, or 0.03 or more, and is, for example, 1.0 or less, 0.4 or less, 0.3 or less, or 0.2 or less. Note that the method of measuring the infrared absorption spectrum (also referred to as infrared spectrum, IR spectrum, or simply as IR) and the measuring device for the infrared absorption spectrum are not particularly limited, and are, for example, as those described in the following examples. Further, in the lens to be fitted to an eye of the present invention, for example, even if the polymer is other than polypropylene, hydrophilization of the surface can be observed by the infrared absorption spectrum. Specifically, for example, the infrared absorption spectrum of the surface of the lens to be fitted to an eye of the present invention may be measured and compared with the infrared absorption spectrum of the non-hydrophilized surfaces of the polymer. Thereby, for example, introduction of a hydrophilic group or the like into the surface of the lens to be fitted to an eye of the present invention can be observed. The polymer is not particularly limited, and is, for example, as described above, and may be, for example, a silicone hydrogel or the like.

While the lens to be fitted to an eye of the present invention contains one element ($\alpha$) selected from the group consisting of Group 15 elements and Group 16 elements, and a Group 17 element ($\beta$), for example, the present invention is not limited thereto. For example, the lens to be fitted to an eye of the present invention may not contain the Group 17 element ($\beta$). Note that the Group 15 element is, for example, at least one of N and P. The Group 16 element is, for example, at least one selected from the group consisting of O, S, Se, and Te. The Group 17 element is, for example, halogen, and is, for example, at least one selected from the group consisting of F, Cl, Br, and I.

Conventionally, as a method for altering a polymer such as polyethylene or polypropylene, for example, a method of introducing maleic anhydride using a radical reaction has been known. However, in such a conventional method, for example, under commercially suitable conditions, a cross-linking reaction or a decomposition reaction may occur simultaneously in the polymer, and an introduction rate of maleic anhydride into a lens to be fitted to an eye is often kept to only about several % by weight. It is preferable that the introduction rate of the functional group of the polymer of the present invention is equal to or higher than that of such an example.

In the lens to be fitted to an eye of the present invention, each of the element ($\alpha$) and the Group 17 element ($\beta$) may be contained as a functional group, for example. Examples of the functional group containing the element ($\alpha$) may include a hydroxyl group, a carbonyl group, and an amide group, and examples of the functional group containing the Group 17 element ($\beta$) may include a chlorine group, a bromine group, an iodine group, an alkyl chloride group, an alkyl bromide group, and an alkyl iodide group.

In the lens to be fitted to an eye of the present invention, a polymer (also referred to as a polymer skeleton) containing the element ($\alpha$) and the Group 17 element ($\beta$) is, for example, a polymer containing carbon and hydrogen and having a carbon-hydrogen bond. Regarding the polymer, for example, reference can be made to the description of the hydrophilization treatment step, and examples of the polymer include polyolefin, polyester, and polycarbonate, as described above. The polyolefin may be, for example, polyethylene, polypropylene, or the like, and the polyester may be, for example, polylactic acid.

Regarding the form of the lens to be fitted to an eye of the present invention, for example, reference can be made to the description as to the hydrophilization treatment step.

The lens to be fitted to an eye of the present invention can be produced as described above, for example, by the hydrophilization treatment step or by a method including other steps (e.g., the functional group introducing step, the agent carrying step).

Note that the type of the lens to be fitted to an eye of the present invention is not particularly limited, and the lens to be fitted to an eye may be, for example, the ocular surface lens or the intraocular lens as described above. The ocular surface lens may be, for example, the detachable contact lens. Further, the intraocular lens may be, for example, the intraocular contact lens or the artificial crystalline lens.

For example, when the lens to be fitted to an eye of the present invention is the detachable contact lens, a method of using the lens is not particularly limited, and may be, for example, a method similar to that of a general detachable contact lens. When the contact lens of the present invention is a silicone hydrogel contact lens, for example, as described above, it has an advantage of a conventional silicone hydrogel contact lens and is stable and less likely deteriorated in a long period of time. Thus, the detachable contact lens of the present invention can have a higher convenience than a general detachable contact lens. Further, for example, as described above, the detachable contact lens of the present invention may or may not carry an agent. When an agent is carried on the detachable contact lens of the present invention, for example, an effect corresponding to the type of the agent can be obtained by sustained-release of the agent.

When the lens to be fitted to an eye of the present invention is the intraocular lens, for example, an agent can be carried as described above. By sustained-release of the agent, an effect corresponding to the type of the agent can be obtained. More specifically, for example, as described above, by carrying a bactericide, an antibacterial agent, or the like, it is possible to prevent an infectious disease after implantation of the intraocular lens. Note that the above description is illustrative, and the intraocular lens of the present invention is not limited thereto. For example, the intraocular lens of the present invention may or may not carry an agent. The method of using the intraocular lens of the present invention is not particularly limited, and for example, a method similar to that of a general intraocular lens may be used.

EXAMPLES

Next, examples of the present invention will be described. It is to be noted, however, that the present invention is by no means limited to the following examples.

Reference Example A

As Reference Example A, alteration treatment (hydrophilization treatment step) using a liquid reaction system was performed.

Reference Example A1

A fluorous solvent ($CF_3(CF_2)_4CF_3$) was used as an organic phase. On the other hand, sodium chlorite ($NaClO_2$) as a dioxide radical generation source and HCl as an acid were dissolved in an aqueous solvent ($H_2O$), thereby preparing an aqueous phase. In the aqueous phase, the final concentration of sodium chlorite was 500 mmol/l, and the final concentration of HCl was 500 mmol/l. 2 ml of the aqueous phase and 5 ml of the organic phase were placed in the same reaction container and brought into contact with each other to form a two-phase reaction system. In the two-phase reaction system, the fluorous solvent as the organic phase was a lower layer, and the aqueous phase was an upper layer. Then, a polypropylene film was put into the reaction container. The film was submerged in the organic phase of the lower layer. The size of the film was 50 mm in length, 20 mm in width, and 0.2 mm in thickness. Note that the film was formed by heat pressing 3 g of polypropylene pellet (trade name: prime Polypro®, manufactured by Prime Polymer Co., Ltd.) at 160° C. and 20 MPa for 10 minutes. Then, in the atmosphere, the two-phase reaction system was irradiated with light at room temperature (about 25° C.) for 30 minutes with an LED lamp (60 W, manufactured by PiPhotonics, Inc.) having a wavelength of $\lambda > 360$ nm, without pressurizing or decompressing. The entire surface of the film in the organic phase was irradiated with light from the sides of the organic phase. At this time, since the color of the organic phase was discolored to yellow, it could be verified that the chlorine dioxide radical generated in the aqueous phase was dissolved in the organic phase. Then, after 30 minutes from the start of the light irradiation, the yellow coloration of the organic phase disappeared, thereby completing the reaction.

Figure 2A:
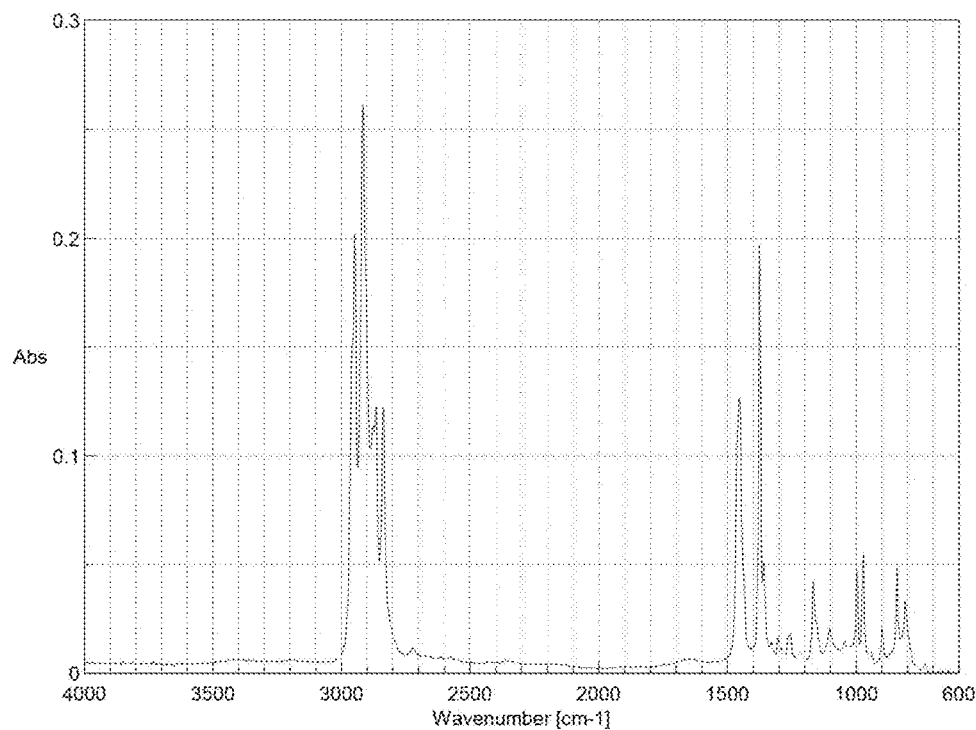
FIGS. 2A and 2B are graphs showing the results of IR of Reference Example A1.
Figure 2B:
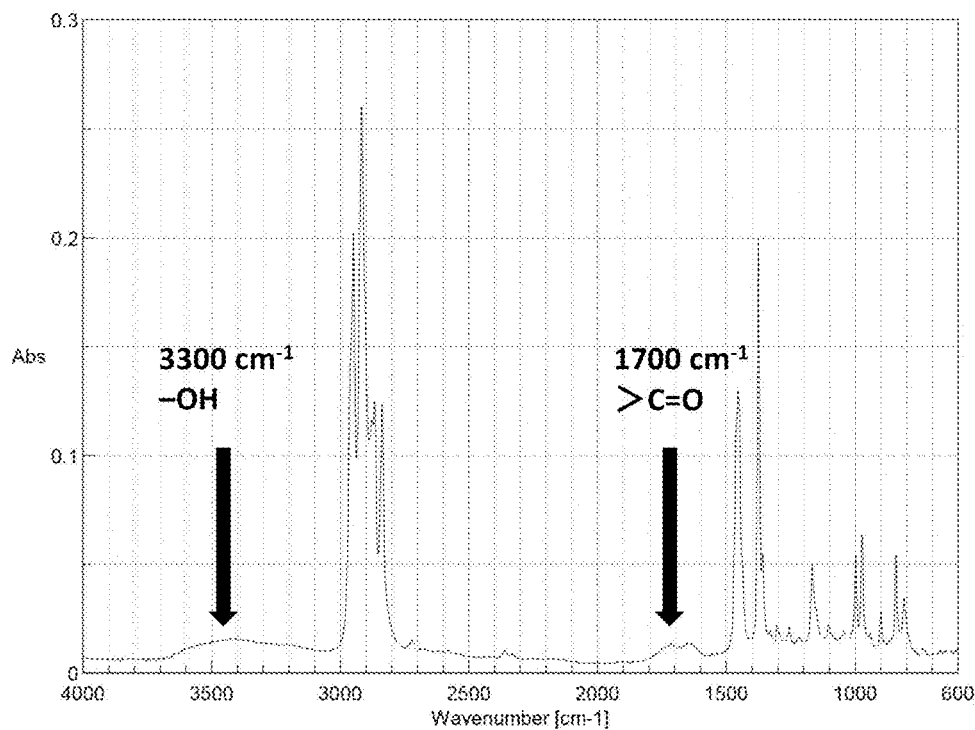

After the light irradiation, IR was performed on the surface of the film that has been irradiated with light. As a comparative example, IR was performed on the film in the same manner before being irradiated with light. The results are shown in FIGS. 2A and 2B. FIG. 2A shows the result before the light irradiation, and FIG. 2B shows the result after the light irradiation. In the present reference example and all of the following reference examples and examples, FT/IR-4700 (trade name, manufactured by JASCO Corporation) with ATR PRO ONE (trade name, manufactured by JASCO Corporation) and a diamond prism attached was used as an IR spectrometer.

As shown in FIG. 2B, owing to the light irradiation, a peak showing a hydroxyl group (—OH) and a peak showing a carbonyl group (—C(=O)—) contained in a carboxyl group (—COOH), which were not observed in FIG. 2A showing the results before the light irradiation, were observed. This result shows that, in the polypropylene film, a methyl group of the side chain of the polymer is oxidized to a hydroxymethyl group (—$CH_2OH$) and a carboxy group (—COOH), and the surface of the film is altered.

Reference Examples B

As Reference Examples B, alteration treatment (hydrophilization treatment step) using a gas phase reaction system was performed.

Reference Example B1

4 ml of fluorous solvent ($CF_3(CF_2)_4CF_3$), 2 ml of water ($H_2O$), 90 mg of sodium chlorite ($NaClO_2$), and 20 µl of 35% hydrochloric acid (HCl) were placed in the same reaction container and stirred for 5 minutes. The reaction container was allowed to stand still, thereby separating into the fluorous solvent as an organic phase, an aqueous phase, and a gas phase from the bottom. Since the organic phase became yellow, it was verified that white gas was generated in the gas phase. The chlorine dioxide radicals are generated in the aqueous phase and are dissolved in the more stable organic phase (fluorous solvent). That is, the change of color of the organic phase into yellow represents the generation of a chlorine dioxide radical, and thus the generation of the chlorine dioxide radical was verified in the present reference example. When the dissolution into the organic phase exceeds a limit amount, the chlorine dioxide radical flows out into the gas phase as a white gas. That is, since the generation of the white gas in the gas phase represents the presence of the chlorine dioxide radical in the gas phase, it was verified that the chlorine dioxide radical was present in the gas phase in the present reference example.

Figure 3:
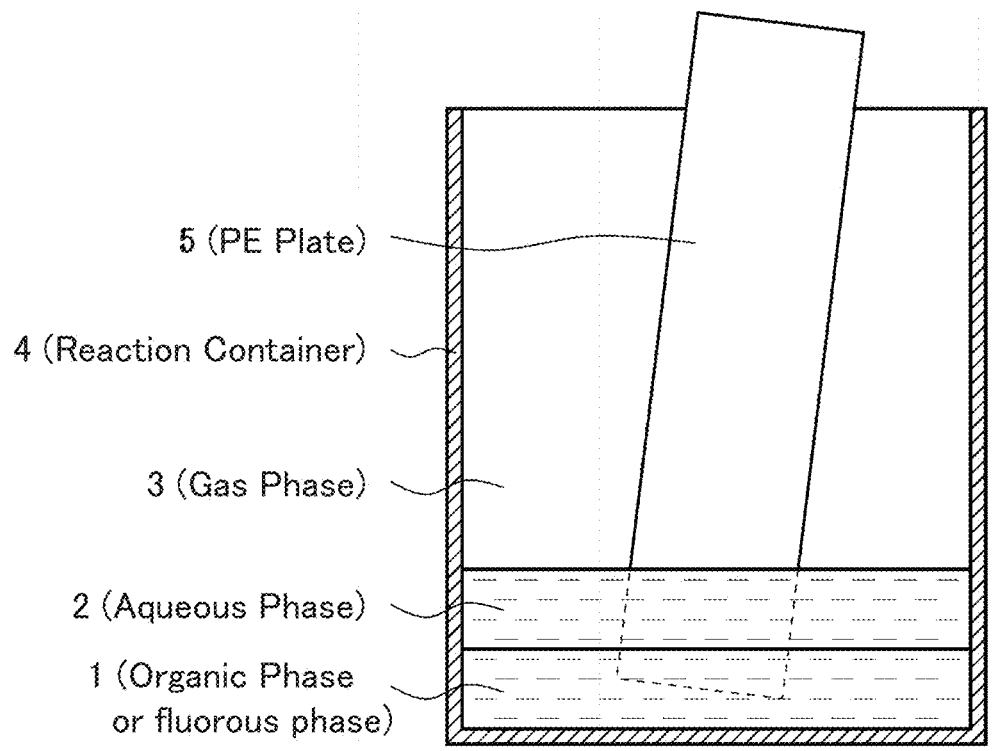
FIG. 3 is a cross-sectional view schematically showing a state of a hydrophilization treatment step in Reference Example B1.

Next, a polyethylene plate (product No.: 2-9217-01, AS ONE Corporation) was put into the reaction container. The size of the polyethylene plate was 50 mm in length, 15 mm in width, and 1 mm in thickness. FIG. 3 is a schematic diagram showing a state in which the polyethylene plate is put in the reaction container. As shown in FIG. 3, in the reaction container 4, the organic phase (fluorous phase) 1, the aqueous phase 2, and the gas phase 3 were separated in this order, and the lower part of the polyethylene plate (PE plate) 5 was immersed in the organic phase 1, and the upper part of the polyethylene plate 5 was exposed to the gas phase 3. Then, the reaction container was made to be an open system without covering the upper part thereof, and was irradiated with light in the atmosphere at room temperature (about 25° C.) with a xenon lamp (500 W, manufactured by USHIO INC., attached with Pyrex® glass filter) having a wavelength of $\lambda > 290$ nm without pressurizing or decompressing the inside of the reaction container. It was observed that, during the light irradiation, the white gas was constantly generated in the gas phase 3, the chlorine dioxide radical was generated in the aqueous phase 2, the generated chlorine dioxide radical exceeded the dissolution limit to the organic phase 1, and excessive chlorine dioxide radical flowed out into the gas phase 3. As to the light irradiation, the surface of the polyethylene plate exposed to the gas phase in the reaction container 4 was irradiated with light. Specifically, parallel light was emitted to the surface of the polyethylene plate 5 so as to be perpendicular to the surface from a distance of 25 cm. Then, after 30 minutes from the start of the light irradiation, the yellow coloration of the organic phase disappeared, thereby completing the reaction.

After the light irradiation, infrared spectroscopy (IR) was performed on the surface of the polyethylene plate that has been irradiated with light. As a comparative example, IR was performed on the polyethylene plate in the same manner before being irradiated with light. As a result, owing to the light irradiation, a peak (around 1700 $cm^{-1}$) showing a carboxy group (—COOH), which was not observed before the light irradiation, was observed. This result shows that, in the polyethylene plate, the C—H bond of polyethylene (around 2900 $cm^{-1}$) was oxidized to a carboxy group (around 1700 $cm^{-1}$) and the surface of the polyethylene plate was altered.

Reference Example B2

Alteration treatment (hydrophilization treatment step) using a gas phase reaction system was performed in the same manner as in Reference Example B1 except that polypropylene was used instead of the polyethylene.

(1) Polypropylene Film

Instead of the polyethylene plate, a polypropylene film was used. The polypropylene film was formed by heat pressing 3 g of polypropylene pellet (trade name: prime Polypro®, manufactured by Prime Polymer Co., Ltd.) at 160° C. and 20 MPa for 10 minutes. The polypropylene film was cut to a size having a length of 50 mm, a width of 15 mm, and a thickness of 0.3 mm. After the light irradiation, IR was performed on the surface of the polypropylene film that has been irradiated with light in the same manner as in Reference Example B1. As a comparative example, IR was performed on the polypropylene film in the same manner before being irradiated with light. As a result, owing to the light irradiation, a peak (around 2900 $cm^{-1}$) showing a carboxy group (—COOH), which was not observed before the light irradiation, was observed. This result shows that, in the polypropylene film, the methyl group (—$CH_3$) of the side chain of polypropylene (around 2900 $cm^{-1}$) and the C—H bond contained in the main chain of polypropylene (around 2900 $cm^{-1}$) were oxidized to a carboxy group (—COOH) (around 1700 $cm^{-1}$), and the surface of the polypropylene film was altered.

Reference Example B3

Alteration treatment (hydrophilization treatment step) using a gas phase reaction system was performed in the same manner as in Reference Example B1 except that a polymethylmethacrylate (PMMA) plate was used instead of the polyethylene plate.

The size of the PMMA plate (product No.: 2-9208-01, AS ONE Corporation) used was 50 mm in length, 15 mm in width, and 1 mm in thickness. After the light irradiation, IR was performed on the surface of the PMMA plate that has been irradiated with light in the same manner as in Reference Example B1. As a comparative example, IR was performed on the PMMA plate in the same manner before being irradiated with light. As a result, after the light irradiation, the vicinity of the 1700 $cm^{-1}$ was widely increased as compared to before the light irradiation, and the broadening of the shoulder peak was observed. The peak corresponds to a carbonyl group (—C(=O)—) contained in an ester group (—COOR), a carboxy group (—COOH), or the like. This result shows that, in the PMMA plate, a C—H bond contained in a methyl group (—$CH_3$) or the like of the side chain of the PMMA was oxidized to a carboxy group (—COOH), and the surface of the PMMA plate was altered.

Reference Example B4

Alteration treatment (hydrophilization treatment step) using a gas phase reaction system was performed in the same manner as in Reference Example B1 except that a polydimethylsiloxane (PDMS) film was used instead of the polyethylene plate.

The PDMS film (trade name: Sylgard 184, manufactured by Dow Corning Toray Co., Ltd.) used was 40 mm in length, 15 mm in width, and 1 mm in thickness. After the light irradiation, IR was performed on the surface of the PDMS film that has been irradiated with light in the same manner as in Reference Example B1. As a comparative example, IR was performed on the PDMS film in the same manner before being irradiated with light. As a result, a peak around 1700 $cm^{-1}$ was not observed before the light irradiation, whereas a peak around 1700 $cm^{-1}$ was observed after the light irradiation. The peak corresponds to a carboxy group (—COOH). This result shows that, in the PDMS film, the methyl group (—$CH_3$) of the side chain of the PDMS (peak around 2900 $cm^{-1}$) and the C—H bond of the main chain of the PDMS (peak around 2900 $cm^{-1}$) were oxidized to a carboxy group (—COOH) (peak around 1700 $cm^{-1}$), and the surface of the PDMS film was altered.

Reference Example B5

Alteration treatment (hydrophilization treatment step) using a gas phase reaction system was performed in the same manner as in Reference Example B1 except that a polycarbonate (PC) plate was used instead of the polyethylene plate.

The polycarbonate (PC) plate (product No.: 2-9226-01, AS ONE Corporation) used was 50 mm in length, 15 mm in width, and 1 mm in thickness. After the light irradiation, IR was performed on the surface of the PC plate that has been irradiated with light in the same manner as in Reference Example B1. As a comparative example, IR was performed on the PC plate in the same manner before being irradiated with light. As a result, after the light irradiation, the vicinity of the 1700 $cm^{-1}$ was widely increased as compared to before the light irradiation, and the broadening of the shoulder peak was observed. The peak corresponds to a carbonyl group (—C(=O)—) contained in a carbonate group (—O—(C=O)—O—), a carboxy group (—COOH), or the like. This result shows that, in the PC plate, a C—H bond contained in a methyl group (—$CH_3$) or the like of the side chain of the PC plate was oxidized to a carboxy group (—COOH), and the surface of the PC plate was altered.

Reference Example B6

Alteration treatment (hydrophilization treatment step) using a gas phase reaction system was performed in the same manner as in Reference Example B1 except that a liquid crystal polymer (LCP) plate (liquid crystal polyester) was used instead of the polyethylene plate.

The LCP plate (trade name: 6030 g-mf, manufactured by UENO FINE CHEMICALS INDUSTRY. LTD.) used was 50 mm in length, 15 mm in width, and 1 mm in thickness. After the light irradiation, IR was performed on the surface of the LCP plate that has been irradiated with light in the same manner as in Reference Example B1. As a comparative example, IR was performed on the LCP plate in the same manner before being irradiated with light. As a result, after the light irradiation, the vicinity of the 1700 $cm^{-1}$ was widely increased as compared to before the light irradiation, and the broadening of the shoulder peak was observed. The peak corresponds to a carbonyl group (—C(=O)—) contained in an ester group (—COOR), a carboxy group (—COOH), or the like. This result shows that, in the LCP plate, a C—H bond contained in the LCP was oxidized to a carboxy group (—COOH) and the surface of the LCP plate was altered.

Reference Example B7

Figure 4:
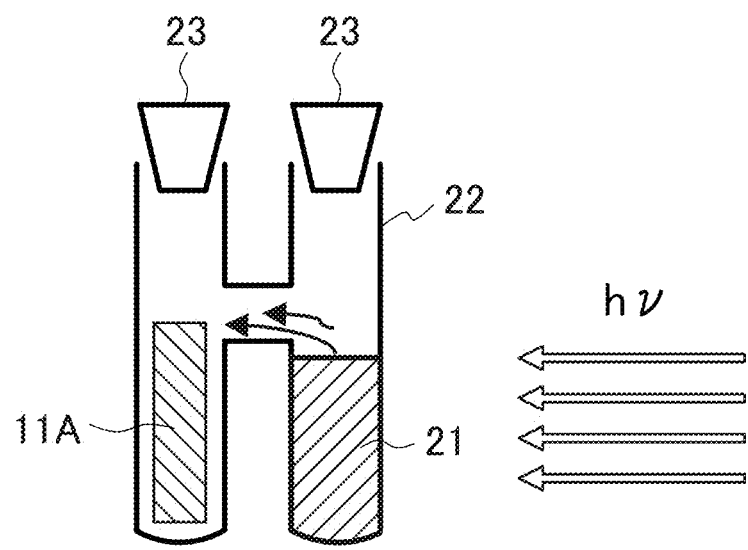
FIG. 4 is a perspective view showing the configuration of a reaction system of Reference Example B7.

A polypropylene (PP) film was subjected to alteration treatment (hydrophilization treatment step) in a gas phase reaction system using a reaction system shown in a perspective view of FIG. 4.

Reference Example B7-1

As shown in FIG. 4, as a reaction container 22, an H-shaped container having two cylindrical containers connected by a passage was used. The reaction container 22 was made of glass, and the two cylindrical containers each had an inner diameter of 10 mm and a depth of 70 mm. The passage was 8 mm in inner diameter and 15 mm in length, and the depth from the bottom inside the passage to the bottom inside each of the cylindrical containers was 50 mm.

As shown in FIG. 4, an acidic aqueous hydrochloric acid ($NaClO_2$) solution 21 was placed in one of the cylindrical containers of the reaction container 22, and a PP film (polymer) 11A was placed in the other cylindrical container. As the acidic aqueous hydrochloric acid ($NaClO_2$) solution 21, an aqueous solution obtained by mixing $H_2O$ (7 ml), $NaClO_2$ (50 mg), and 35% HClaq. (50 µl) was used. As the PP film 11A, used was a film obtained by cutting the same PP film as that used in Reference Example B2 into 50 mm in length, 10 mm in width, and 0.2 mm in thickness. In this state, the reaction container 22 was sealed with a lid 23, and the acidic aqueous hydrochloric acid ($NaClO_2$) solution 21 was then irradiated with light at the power of 60 W from the side surface of the reaction container 22 for 5 minutes. A light source used was an LED lamp with a wavelength of 365 nm. The distance between the light source and the reaction container 22 was 20 cm. Chlorine dioxide radicals generated by the light irradiation were reacted with the surface of the PP film 11A to conduct hydrophilization treatment. The reaction was carried out in atmosphere at room temperature, without pressurization and decompression. The reaction was completed when the yellow coloration of the $NaClO_2$ solution derived from the $ClO_2$ radicals disappeared. After completion of the reaction, the PP film 11A was washed with purified water and dried under reduced pressure overnight. In this manner, the alteration treatment (hydrophilization treatment step) of the PP film 11A was performed.

Reference Example B7-2

APP film 11A was subjected to alteration treatment (hydrophilization treatment step) in the same manner as in Reference Example B7-1 except that the cylindrical container containing the PP film 11A in the reaction container 22 was covered with aluminum to shield from light, so that the PP film 11A was not exposed to light. Specifically, in the present example, the hydrophilization treatment step was performed with the reaction system in the hydrophilization treatment step (the cylindrical container containing the PP film 11A in the reaction container 22) not irradiated with light and only the radical generation reaction system (the cylindrical container containing the acidic aqueous hydrochloric acid ($NaClO_2$) solution 21 in the reaction container 22) irradiated with light.

IR Spectrum Measurement

IR spectra (infrared absorption spectra) were measured for the PP films 11A of Reference Example B7-1 and Reference Example B7-2 before the reaction (before the hydrophilization treatment step) and after the reaction (after the hydrophilization treatment step). The conditions for IR measurement are the same as described above. As a result, in both of Reference Examples B7-1 and B7-2, the peak intensity at around 2900 $cm^{-1}$ was decreased and the peak intensity at around 1700 $cm^{-1}$ was increased after the reaction as compared to those before the reaction. This result implies that the methyl group on the surface of the PP film 11A was oxidized into the carboxy group. Further, Reference Example B7-2 demonstrates that, in the hydrophilization treatment step, the reaction proceeds without irradiation of the reaction system of the hydrophilization treatment step with light.

The results of the measurement of the IR spectrum of Reference Example B7-1 are summarized in Table 4 below. Table 4 shows the measurement results of the PP film 11A before the reaction as a control together with the results of changes in reaction time of the hydrophilization treatment step to 10 minutes and 60 minutes. As can be seen from Table 4 below, the ratio C=O/C—H of an area of a peak derived from C=O expansion and contraction in 1700 to 1800 $cm^{-1}$ to an area of a peak derived from C—H expansion and contraction in 2800 to 3000 $cm^{-1}$ was considerably increased as compared to the area before the reaction at the reaction time of both 10 minutes and 60 minutes.

TABLE 4

|  | C = O peak area (1700 to 1800 $cm^{-1}$) | C-H peak area (2800 to 3000 $cm^{-1}$) | C = O/C-H |
|---|---|---|---|
| Before reaction | 0.064 | 19.3 | 0.003 |
| 10 min | 0.84 | 22.1 | 0.038 |
| 60 min | 0.71 | 21.9 | 0.032 |

Measurement of Contact Angle with Water

The contact angles of the PP films of Reference Examples B7-1 and B7-2 with water were measured using Drop Master DM300 (trade name, manufactured by Kyowa Interface Science Co., Ltd.). In the above measurement, 1 microliter of pure water was added dropwise on the surface of the object to be measured, and the contact angle after 2 seconds of the addition was calculated by a static contact angle method using FAMAS (trade name, manufactured by Kyowa Interfacial Science Co., Ltd.) as analysis software. In all of the following reference examples and examples, the contact angle with water was measured by the same method using the same device as in the present reference example.

The measurement results of the contact angle with water in Reference B7-1 are summarized in Table 5 below. Table 5 also shows the measurement results of the PP film 11A before the reaction as a control together with the results of changes in reaction time of the hydrophilization treatment step to 10 minutes and 60 minutes. As can be seen from Table 5 below, the contact angle was about 20° or more smaller than that before the reaction at both 10 and 60 minutes of the reaction time. It was thus demonstrated that hydrophilicity of the PP film 11A was increased by the hydrophilization treatment step.

TABLE 5

|  | Contact angle |
|---|---|
| Before reaction | 107° |
| 10 min | 88° |
| 60 min | 83° |

Tables 6 and 7 below show the results of the IR measurement and the measurement of the contact angle with water of the PP films of Reference Example B7-1 (with irradiation of the PP film 11A with light) and Reference Example B7-2 (without irradiation of the PP film 11A with light). In Tables 6 and 7, the reaction time for the hydrophilization treatment step was 10 minutes. As can be seen from Tables 6 and 7 below, neither Reference Examples B7-1 nor B7-2 changed the C=O/C—H and the contact angle with water. This demonstrates that, in the hydrophilization treatment step, the number of C=O bonds and hydrophilicity were increased without irradiation of the PP film 11A with light as well as with the irradiation.

TABLE 6

| | C = O peak area (1700 to 1800 cm$^{-1}$) | C-H peak area (2800 to 3000 cm$^{-1}$) | C = O/C-H |
|---|---|---|---|
| With light irradiation | 0.84 | 22.1 | 0.038 |
| Without light irradiation | 0.79 | 22.7 | 0.035 |

TABLE 7

| | Contact angle |
|---|---|
| With light irradiation | 88° |
| Without light irradiation | 89° |

Reference Example B8

A polylactic acid (PLA) film was subjected to alteration treatment (hydrophilization treatment step) in a gas phase reaction system in the following manner.

An acidic aqueous hydrochloric acid (NaClO$_2$) solution was placed in a small petri dish (30 mm in diameter×10 mm in depth) as a reaction container. As the acidic aqueous hydrochloric acid (NaClO$_2$) solution, an aqueous solution obtained by mixing H$_2$O (7 ml), NaClO$_2$ (1000 mg), and 35% HClaq. (1000 µl) was used. This small petri dish and the polylactic acid (PLA) film were placed in a large petri dish (700 mm in diameter×180 mm in depth). The polylactic acid (PLA) film was obtained by heat pressing 3 g of polylactic acid pellets (trade name: 2003D®, manufactured by Nature Works) at 170° C. and 10 MPa for 10 minutes. The PLA film cut into 50 mm in length, 10 mm in width, and 0.3 mm in thickness was used. Thereafter, the large petri dish was covered with a lid and pre-heated at 70° C. for 5 minutes. Then, while the heating was continued, light at the power of 60 W was applied from above the lid for 5 minutes. A light source used was an LED lamp with a wavelength of 365 nm. The distance between the light source and the large petri dish was 20 cm. Chlorine dioxide radicals generated by the light irradiation were hydrophilized by reacting with the surface of the PLA film. The reaction was carried out in atmosphere at room temperature, without pressurization and decompression. The reaction was completed when the yellow coloration of the NaClO$_2$ solution derived from the ClO$_2$ radicals disappeared. After completion of the reaction, the PLA film was washed with purified water and dried under reduced pressure overnight. In this manner, the PLA film was subjected to alteration treatment (hydrophilization treatment step).

Under the reaction conditions of the hydrophilization treatment step, the reaction was performed with the change in reaction time to 0 minutes (i.e., unreacted), 10 minutes, and 30 minutes, and then the IR measurement was performed. The conditions for IR measurement were the same as described above. The result shows that, by the hydrophilization treatment step, hydrophilic functional groups such as an alcoholic hydroxyl group (C—OH) and a carboxy group (COOH) were increased on the surface of the PLA film.

Reference Example B9

Alteration treatment (hydrophilization treatment step) using a gas phase reaction system was performed in the same manner as in Reference Example B8, except that an ABS resin film was used instead of a polylactic acid (PLA) film. Further, it was examined that the surface was altered (oxidized) to increase the hydrophilic functional group by the same method as Reference Example B8.

Reference Example B10

The surface of the polypropylene (PP) plate was subjected to alteration treatment (hydrophilization treatment step) by selectively reacting with a halogen oxide radical. It was examined that the surface of the PP plate has selectively oxidized (altered) by binding toluidine blue to the surface.

Figure 5A:
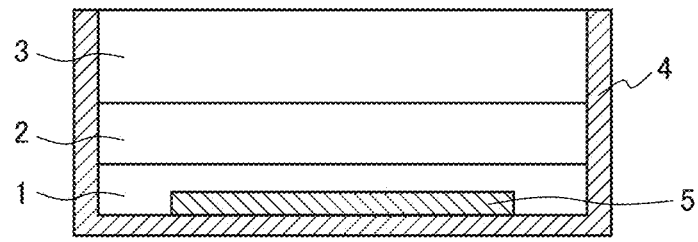
FIGS. 5A and 5B are diagrams schematically showing a reaction container and a plate in Reference Example B10.

A transparent petri dish, which is a reaction container, was filled with 10 ml of fluoras solvent (CF$_3$(CF$_2$)$_4$CF$_3$), 20 ml of water (H$_2$O), 200 mg of sodium chlorite (NaClO$_2$), and 200 µl of 35% hydrochloric acid (HCl), and stirred for 5 minutes. The reaction container was allowed to stand to separate the fluorous solvent into an organic phase, an aqueous phase, and a gas phase from the bottom. It was observed that ClO$_2$ radicals generated in the aqueous phase were transferred to the organic phase by checking the organic phase being colored yellow. Next, a PP plate (product number 2-9221-01 manufactured by AS ONE Corporation.) was introduced into the reaction container. The size of the PP plate was 50 mm in length, 30 mm in width, and 1 mm in thickness. FIG. 5A is a schematic diagram showing a state where the PP plate is placed in the reaction container. In the reaction container 4, the organic phase 1, the aqueous phase 2, and the gas phase 3 were separated in this order, and the PP plate 5 was immersed in the organic phase 1.

Figure 5B:
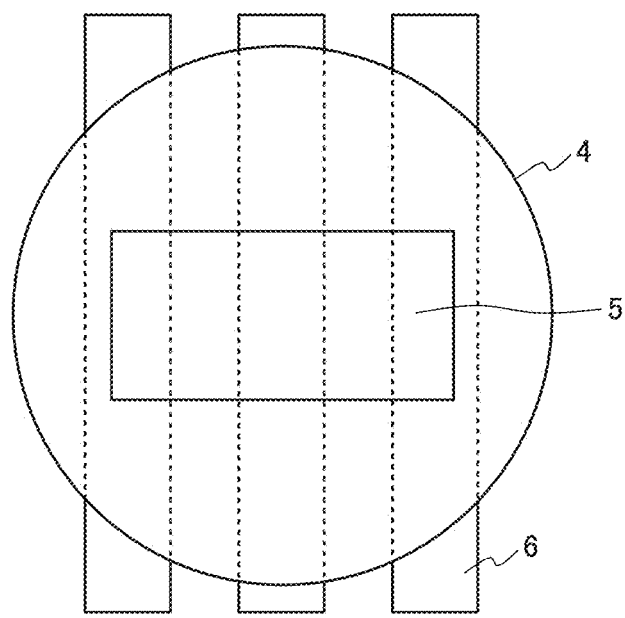

Then, a lid was placed on the upper portion of the reaction container. A light source was disposed below a transparent table so as to face upward, and three black rectangular papers as masking members were disposed on the transparent table at regular intervals. The reaction container was disposed on the masking member. FIG. 5B shows the positional relationship among the reaction container 4, the PP plate 5, and the masking member 6. FIG. 5B is a plan view of the reaction container 4 as seen from above. Light irradiation was performed from the light source below the transparent table toward the reaction container on the transparent table. Since the masking member is disposed under the reaction container, the lower surface of the PP plate in the reaction container is irradiated with light only at a site where the masking member is not disposed. The distance between the light source and the PP plate was 20 cm. As the light source, an LED lamp (Biophotonics) with a wavelength of 365 nm was used. The light irradiation was performed at room temperature (about 25° C.) without pressurizing or decompressing the reaction container in an atmosphere. Then, after 30 minutes from the start of light irradiation, the reaction was terminated by confirming the disappearance of the yellow coloration derived from ClO$_2$ radicals in the organic phase in the reaction container.

Next, 50 ml of 0.05% toluidine blue aqueous solution of the blue dyes was prepared, and then the PP plate that has been oxidized by ClO$_2$ radicals was placed. After sonication for 1 minute at room temperature, the PP plate was taken out and washed with water.

Figure 6:
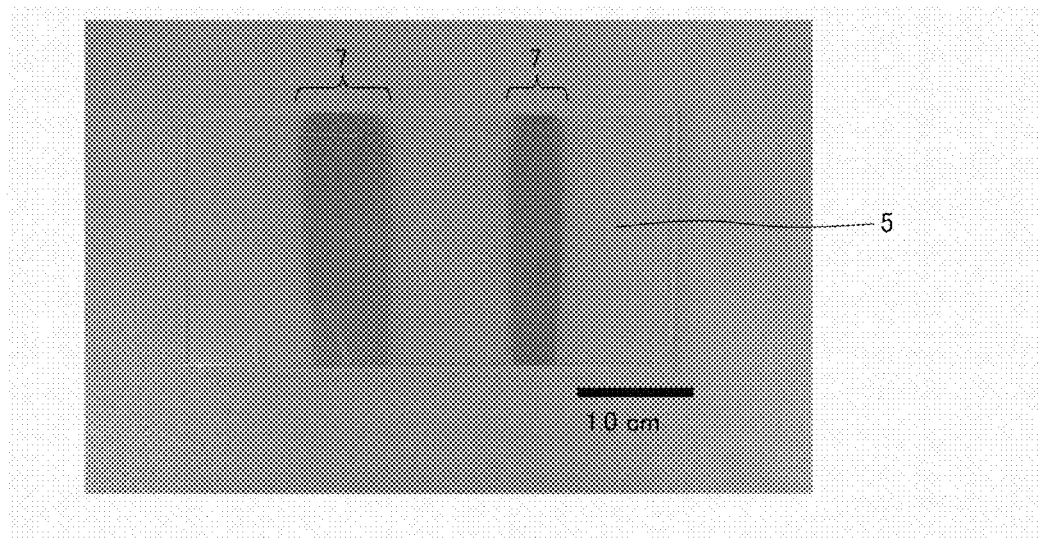
FIG. 6 is a photograph showing the coloring results in Reference Example B10.

FIG. 6 shows a photograph of the obtained PP plate. As shown in FIG. 6, in the PP plate 5, it was observed that toluidine blue was bound only to a site 7 where the masking member 6 was not disposed. Despite the fact that the toluidine blue aqueous solution was brought into contact with the entire surface of the PP plate 5, binding of toluidine blue was observed only in a region where the masking member 6 was not disposed. This shows that, by selectively irradiating light by masking in the presence of $ClO_2$ radicals, only the region where the masking member was not disposed was oxidized (hydrophilized).

By performing the same treatment as in the present reference example using a polypropylene (PP) particle, a polypropylene (PP) film, a substantially cylindrical body of a high-density polyethylene (PE) pellet, and a PS (polystyrene) plate instead of the PP plate, it was determined that a selective hydrophilization treatment was possible in the same manner.

Reference Example B11

The PP film was subjected to the alteration treatment (hydrophilization treatment step) in the same manner as in Reference Example B8 except that the same PP film as the PP film 11A of Reference Example B7-1 was used instead of the PLA film and the hydrophilization treatment step was performed while the PP film was heated to keep the reaction temperature at 60° C. or 90° C. Tables 8 and 9 below show the results of the IR measurement and the measurement of the contact angle with water of the PP film that has been subjected to the hydrophilization treatment step together with the results of Reference Example B7-1. "25° C." is the measurement result of the Reference Example B7-1 (without heating). As can be seen from Tables 8 and 9, even in the present reference example in which the hydrophilization treatment step was performed while heating the PP film 11A, it was verified that the number of C=O bonds and the hydrophilicity were increased in the same manner as in Reference Example B7-1 in which heating was not performed.

TABLE 8

|  | C = O peak area (1700 to 1800 $cm^{-1}$) | C-H peak area (2800 to 3000 $cm^{-1}$) | C = O/C-H |
| --- | --- | --- | --- |
| 25° C. | 0.84 | 22.1 | 0.038 |
| 60° C. | 0.76 | 18.8 | 0.040 |
| 90° C. | 3.35 | 17.8 | 0.188 |

TABLE 9

|  | Contact angle |
| --- | --- |
| 25° C. | 88° |
| 60° C. | 100° |
| 90° C. | 95° |

Reference Example B12

The polylactic acid (PLA) film was subjected to the alteration treatment (hydrophilization treatment step) in the same manner as in Reference Example B8 except that the reaction temperature of the hydrophilization treatment step was changed to 25° C. (room temperature), 60° C., 70° C., or 80° C., and the reaction time of the hydrophilization treatment step was fixed to 10 minutes. As a result of performing IR measurement for each of them, it was verified that, by the hydrophilization treatment step, a hydrophilic functional group such as an alcoholic hydroxyl group (C—OH), a carboxy group (COOH), or the like was increased on the surface of the PLA film.

As to the PLA film after each alteration treatment (hydrophilization treatment step), the contact angle with water was measured. The results are shown in Table 10 below. As a control, the measurement result before the reaction (before the hydrophilization treatment step) is also summarized. As can be seen from Table 10, the contact angle with water was greatly reduced as compared to that before the reaction at any reaction temperature, and it was verified that the surface of the PLA film surface has been hydrophilized.

TABLE 10

|  | Contact angle |
| --- | --- |
| Before reaction | 90° |
| 25° C. | 75° |
| 60° C. | 65° |
| 70° C. | 49° |
| 80° C. | 52° |

Reference Example B13

Alteration treatment (hydrophilization treatment step) using a gas phase reaction system was performed in the same manner as in Example B7-1 except that a plate of polycarbonate, ABS resin, polyethylene naphthalate, or polyethylene was used instead of the PP film 11A. The size of each plate was 50 mm in length, 15 mm in width, and 1 mm in thickness. Then, the contact angles of the plate with water before the reaction (before the hydrophilization treatment step) and after the reaction (after the hydrophilization treatment step) were measured. The plates used and the measured values of the contact angle with water are summarized in Table 11 below. As can be seen from Table 11 below, since the contact angle with water became small after the hydrophilization treatment step in all cases, it was verified that the surface of the plate (polymer) has been hydrophilized.

TABLE 11

|  | Contact angle | |
| --- | --- | --- |
|  | Before reaction | After reaction |
| Polycarbonate (AS ONE Corporation., product number: 2-9224-01) | 88° | 64° |
| ABS resin (AS ONE Corporation., product number: 2-9227-01) | 95° | 62° |
| Polyethylene naphthalate (AS ONE Corporation., product number: 3-2162-01) | 90° | 74° |
| Polyethylene (AS ONE Corporation., product number: 2-9215-01) | 91° | 79° |

Reference Example B14

Alteration treatment (hydrophilization treatment step) using a gas phase reaction system was performed in the same manner as in Reference Example B8, except that silicone hydrogel was used instead of a polylactic acid (PLA) film.

Further, it was examined that the surface was altered (oxidatized) to increase the hydrophilic functional group by the same method as Reference Example B8.

The silicone hydrogel was synthesized based on the following chemical reaction formula (3). That is, first, N,N-dimethylacrylamide (DMAAm) was prepared. This was reacted with polydimethylpolysiloxane dimethacrylate (PDMSDMA), which is a crosslinking agent, and azobisisobutyronitrile (AIBN), which is a radical initiator, in a toluene solvent for 4 hours at 65° C. Thereby, a polydimethylsiloxane gel (PDMS gel), which is a kind of silicone hydrogel, was obtained. The obtained PDMS gel was first washed with tetrahydro tetrahydrofuran (THF), and then washed with water to replace the inner solvent, and then allowed to stand and dry, followed by alteration treatment (hydrophilization treatment step). By changing the amount of the crosslinking agent (PDMSDMA) to 0.5 mol %, 1.0 mol %, and 2.0 mol % to synthesize a PDMS gel, it was possible to control the water content of the PDMS gel after drying. As shown in the chemical reaction formula (3), the water content (water content ratio) of the PDMS Gel after drying was 82.5±0.3% when the crosslinking agent (PDMSDMA) was 0.5 ml %, 61.2±0.3% when the crosslinking agent (PDMSDMA) was 1.0 ml %, and 38.5±0.4% when the crosslinking agent (PDMSDMA) was 2.0 ml %. Note that the water content (water content ratio) was calculated from the weight measurement of the gel at the time of water swelling and the weight measurement of the gel after freeze-drying.

Chemical Formula (3)

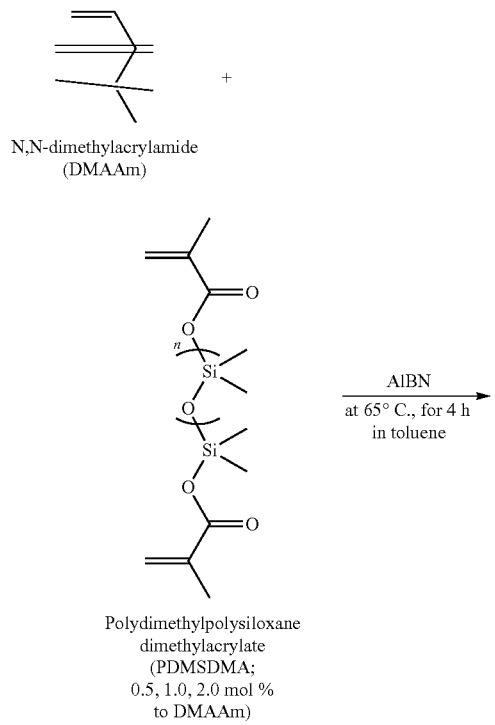

N,N-dimethylacrylamide
(DMAAm)

+

AIBN
at 65° C., for 4 h
in toluene

Polydimethylpolysiloxane
dimethacrylate
(PDMSDMA;
0.5, 1.0, 2.0 mol %
to DMAAm)

-continued

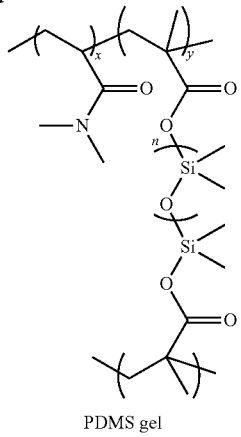

PDMS gel

| Solvent substitution: toluene→THF→water | |
|---|---|
| Cross-linking degree | Water content |
| 0.5 mol % | 82.5 ± 0.3% |
| 1.0 mol % | 61.2 ± 0.3% |
| 2.0 mol % | 38.5 ± 0.4% |

Figure 7A:
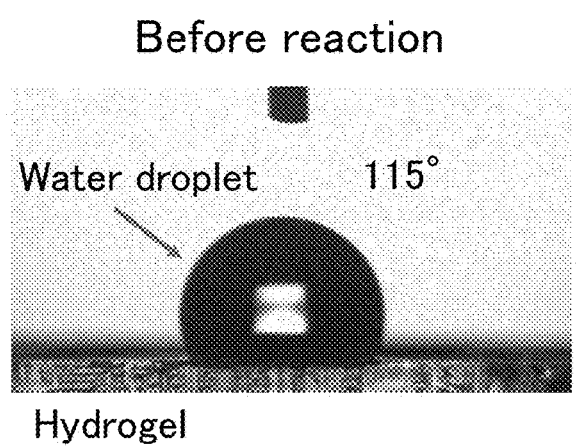
FIGS. 7A and 7B are photographs showing the contact angle with water in silicone hydrogel in Reference Example B14.
Figure 7B:
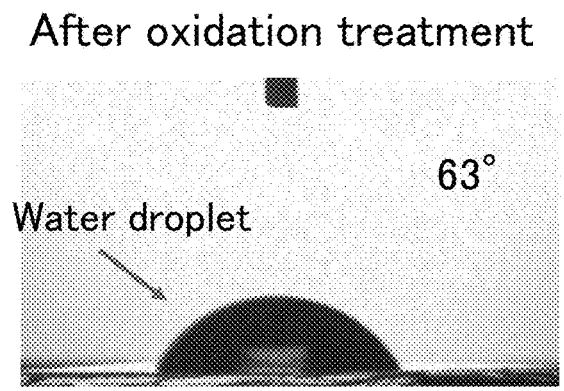

FIGS. 7A and 7B are photographs showing the measurement results of the contact angle with water droplets using the PDMS gel with the crosslinker (PDMSDMA) of 2.0 mol %. FIG. 7A (before reaction) shows the measurement result before performing the alteration treatment (oxidation treatment) by the hydrophilization treatment step. FIG. 7B (after oxidation treatment) shows the measurement result after performing the alteration treatment (oxidation treatment) by the hydrophilization treatment step. As shown in FIGS. 7A and 7B, the contact angle with water droplets before the hydrophilization treatment step was 115° whereas the contact angle with water droplets after the hydrophilization treatment step was 63°, and it was verified that the hydrophilicity became high after the alteration treatment.

Note that, in the present reference example (Reference Example B14), silicone hydrogel in the shape of plate was used from the viewpoint of measuring the contact angle with water droplets as shown in the photographs of FIGS. 7A and 7B. This result shows that an actual silicone hydrogel contact lens can be hydrophilized by performing the hydrophilization treatment step in the same manner.

Reference Example B15

Figure 10:
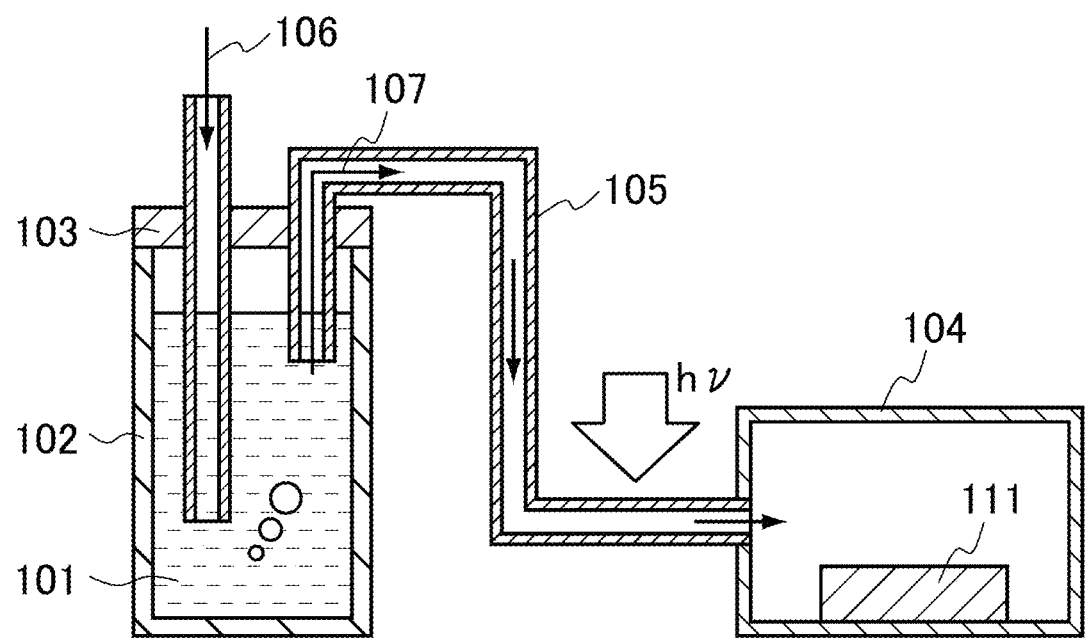
FIG. 10 is a cross-sectional view showing the configuration of a reaction system of Reference Example B15.

A polypropylene (PP) film was subjected to alteration treatment (hydrophilization treatment step) in a gas phase reaction system using a reaction system shown in a cross-sectional view of FIG. 10.

As shown in FIG. 4, a cylindrical container was used as a reaction container 102 for generating chlorine dioxide $ClO_2$. The reaction container 102 was made of glass and had an inner diameter of 100 mm and a depth of 200 mm. Further, a sealed cylindrical container was used as a reaction container 104 for alteration treatment (hydrophilization treatment step) of the polymer. The reaction container 104 was made of glass and had an inner diameter of 200 mm and a depth of 30 mm. Further, a passage 105 connecting the reaction containers 102 and 104 was made of Teflon (trade name: polytetrafluoroethylene) and had an inner diameter of 5 mm and a length of 100 mm.

As shown in FIG. 4, an acidic aqueous hydrochloric acid ($NaClO_2$) solution 101 was placed at the bottom of the reaction container 102, and a PP film (polymer) 111 was placed in the other reaction container 104. As the acidic aqueous hydrochloric acid ($NaClO_2$) solution 101, an aqueous solution obtained by mixing $H_2O$ (50 ml), $NaClO_2$ (200 mg), and 35% HClaq. (100 µl) was used. As the PP film 111, a film obtained by cutting the same PP film as that used in Reference Example B2 into 50 mm in length, 10 mm in width, and 0.2 mm in thickness was used. In this state, the reaction container 102 was sealed with a lid 103. In the acidic aqueous hydrochloric acid ($NaClO_2$) solution 101, $ClO_2$ generated by reacting $NaClO_2$ (200 mg) and HCl with each other is dissolved. In this state, air 106 was blown into the acidic aqueous hydrochloric acid ($NaClO_2$) solution 101 at a flow rate of 0.2 l/min using an air pump as shown in FIG. 4. Accordingly, $ClO_2$ 107 was expelled from the acidic aqueous hydrochloric acid ($NaClO_2$) solution 101 and flowed into the passage 105. In this state, the passage 105 was continuously irradiated with light at the power of 60 W. A light source used was an LED lamp with a wavelength of 365 nm. The distance between the light source and the passage 105 was 20 cm. By this light irradiation, $ClO_2$ was activated to be $ClO_2$ radicals (chlorine dioxide radicals). The chlorine dioxide radicals flowing into the reaction container 104 reacted with the surface of the PP film 111, thereby performing surface treatment. The reaction was carried out in atmosphere at room temperature, without pressurization and decompression. The reaction was completed when the yellow coloration of the $NaClO_2$ solution derived from the $ClO_2$ radicals disappeared. After completion of the reaction, the PP film 111 was washed with purified water and dried under reduced pressure overnight. In this manner, the PP film 111 was subjected to alteration treatment (hydrophilization treatment step).

In this manner, in the present reference example (Reference Example B15), the $ClO_2$ gas was activated by light irradiation to be chlorine dioxide radicals, while a reaction system containing chlorine dioxide radicals (halogen oxide radicals) and the PP film 111 (polymer) was not irradiated with light. Even in the case in which the length of the passage 105 was 1000 mm (1 m), the surface of the PP film 111 could be altered by alteration treatment (hydrophilization treatment step).

Reference Example B16

Alteration treatment (hydrophilization treatment step) of the surface of each of the polymers was performed in the same manner as in Reference Example B1, except that, instead of the polyethylene plate of Reference Example B1, a polymer of any one of acrylonitrile-butadiene-styrene copolymer (ABS), polyacetal (POM), polyethylene (PE), polypropylene (PP), stretched polypropylene, cyclo olefin polymer (COP), polyethylene terephthalate (PET), polyvinyl chloride (PVC), soft PVC, liquid crystal polymer (LCP), polycarbonate (PC), polylactic acid (PLA), polybutylene terephthalate (PBT), tetrafluoroethylene/ethylene copolymer (ETFE), polyphenylene sulfide (PPS), 3-hydroxybutanoic acid/3-hydroxyhexanoic acid copolymer (PHBH), polyetherimide (PEI), polyphenylene ether (PPE), polyether sulfone (PESU), polymethyl methacrylate (PMMA), carbon fiber reinforced plastic (carbon material/epoxy material composite material), high density polyethylene (HDPE), thermoplastic elastomer, ethylene-vinylalcohol copolymer (EVOH), thermoplastic polyurethane elastomer (TPU), polyamide (PA), and ethylene propylene rubber (EPDM) was used. Further, the alteration treatment (hydrophilization treatment step) of the surface of each of the polymers was performed in the same manner as in Reference Example B15 instead of the method of Reference Example B1. It was verified that the surfaces of all of the above polymers were hydrophilized by performing the IR measurement, the measurement of the contact angle with water, or the like in the same manner as in the above described reference examples. In other words, according to the present reference example, it was verified that the surface of each of the above described polymers could be hydrophilized by either of the method of irradiating the polymer surface with light (the method of Reference Example B1) and the method of not irradiating the polymer surface with light (the method of Reference Example B15).

Example 1

Figures 8A, 8B, 8C:
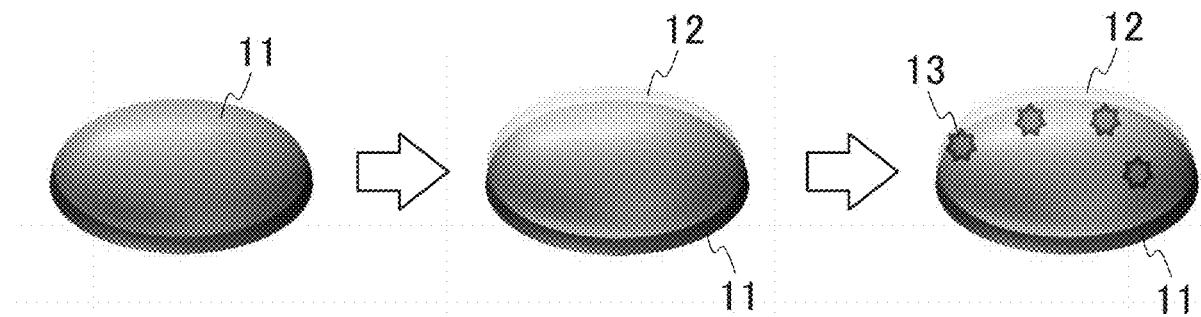
FIG. 8 is a step perspective view illustrating a method for producing a lens to be fitted to an eye of the present invention carrying an agent.

As shown in the schematic diagram of (a) and (b) of FIG. 8, the surface of the intraocular lens was hydrophilized to produce the intraocular lens having a hydrophilized surface. That is, first, as shown in (a) of FIG. 8, a commercially available intraocular lens (made of acrylic resin) was prepared as a polymer lens 11. Then, as shown in (b) of FIG. 8, the surface of the polymer lens 11 was altered by the hydrophilization treatment step to be the altered surface 12, followed by washing with purified water, thereby producing the intraocular lens having a hydrophilized surface.

Note that the same reaction system as in Reference Example B8 was used in the hydrophilization treatment step. The hydrophilization treatment step was performed in the same manner as in Reference Example B8 except that an intraocular lens was used instead of a polylactic acid (PLA) film and that the hydrophilization treatment step was performed at room temperature without preheating by a heater and that the light irradiation time was 5 minutes. Further, it was verified that the surface was altered (oxidized) and the hydrophilic functional group was increased by the same method as in Reference Example B8.

Example 2

As shown in the schematic diagram of (b) and (c) of FIG. 8, the agent was carried on the surface of the intraocular lens produced in Example 1, thereby producing the intraocular lens carrying the agent. Specifically, the aforementioned agent carrying step was carried out by immersing the intraocular lens ((b) of FIG. 8) produced in Example 1 in 10 mM cefotiam hydrochloride (agent) aqueous solution and sonicating for 10 minutes. Thus, as shown in (c) of FIG. 8, the intraocular lens carrying an agent 13 (cefotiam) was produced. Thereafter, the intraocular lens was further immersed in purified water and washed by sonication for 20 minutes, thereby removing excess agent and the like. The chemical structure of the agent (cefotiam HCl) used in the present example is as shown in the chemical formula (4) below.

Chemical Formula (4)

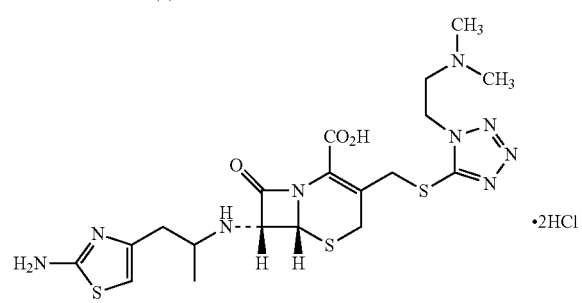

Figure 9:
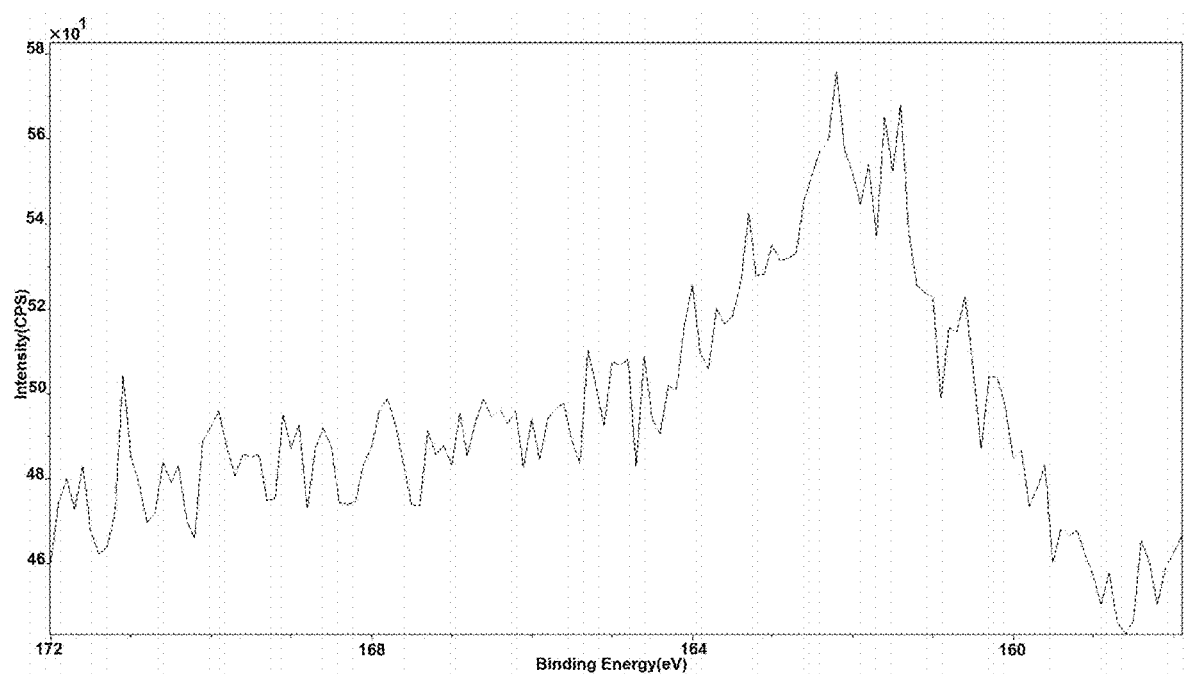
FIG. 9 is an XPS spectrum of an intraocular lens carrying an agent (cefotiam) in Examples.

It was verified that the agent (cefotiam) was carried on the intraocular lens ((c) of FIG. 8) produced in the present example by the XPS spectrum measurement. The XPS method was performed using a commercially available device (trade name: AXIS-NOVA, manufactured by KmtoS) under the measurement conditions as follows: monochromatization AlKa (1486.6 ev) was used as an X-ray source and an analytical area was 300 µm×700 µm (set value). FIG. 9 shows the XPS spectrum (Narrow spectrum). In FIG. 9, the horizontal axis indicates the binding energy (eV) and the vertical axis indicates the relative value of the peak intensity (cps). As shown in FIG. 9, a sulfur atom-derived peak (S1s) was detected within the range of 160 to 164 eV, which shows that an agent (cefotiam) was carried on the surface of the intraocular lens.

The XPS spectra of the polymer lens ((a) of FIG. 8, the commercially available intraocular lens) and the intraocular lens of Example 1 ((b) of FIG. 8, subjected only to the hydrophilization treatment step and not to the agent carrying step) were measured in the same manner. As a result, the sulfur atom-derived peak (S1s) was not detected. This shows that the sulfur atom-derived peak (S1s) was derived from cefotiam.

Example 3

The intraocular lens carrying the agent was produced in the same manner as in Example 2 except that cefmenoxime hydrochloride was used instead of cefotiam hydrochloride. The concentration of the agent (cefmenoxime hydrochloride) aqueous solution in the agent carrying step was set to 10 mM as in Example 2. Further, as in Example 2, the sulfur atom-derived peak (S1s) was detected by the XPS spectrum measurement, and it was verified that the agent (cefmenoxime) was carried on the surface of the intraocular lens. The chemical structural formula of the agent (cefmenoxime hydrochloride) used in the present example is as shown in the following chemical formula (5).

Chemical Formula (5)

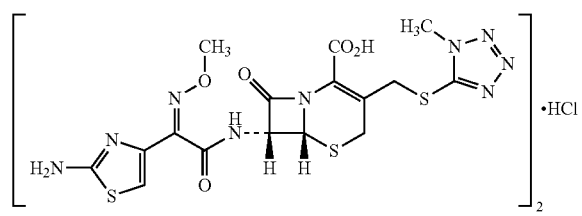

Reference Example B17

The surface of a PMMA plate was altered (hydrophilized) in the following manner, and further, the agent was carried on the surface of the PMMA plate. Further, the sustained-release of the agent was examined for the PMMA plate carrying the agent. In the present reference example (Reference Example B17) and Reference Example B18 described below, levofloxacin was used as the agent.

Hydrophilization Treatment Step

First, as the PMMA plate, prepared the same PMMA plate as that used in Reference Example B3 (product No.: 2-9208-01, AS ONE Corporation 50 mm in length×15 mm in width×1 mm in thickness). On the other hand, an acidic aqueous hydrochloric acid ($NaClO_2$) solution was placed in a small petri dish (30 mm in diameter×10 mm in depth) as a reaction container. As the acidic aqueous hydrochloric acid ($NaClO_2$) solution, an aqueous solution obtained by mixing $H_2O$ (7 ml), $NaClO_2$ (1000 mg), and 35% HClaq. (1000 µl) was used. This small petri dish and the PMMA plate were placed in a large petri dish (700 mm in diameter×180 mm in depth). Thereafter, the large petri dish was covered with a lid and pre-heated at 90° C. for 5 minutes. Then, while the heating was continued, light at the power of 60 W was applied from above the lid for 5 minutes. A light source used was an LED lamp with a wavelength of 365 nm. The distance between the light source and the large petri dish was 20 cm. The PMMA plate was surface-treated by reaction chlorine dioxide radicals generated by the light irradiation with the surface of the PMMA plate. The reaction was carried out in atmosphere at room temperature, without pressurization and decompression. The reaction was completed when the yellow coloration of the $NaClO_2$ solution derived from the $ClO_2$ radicals disappeared. After completion of the reaction, the PMMA plate was washed with purified water and dried under reduced pressure overnight. In this manner, the surface of the PMMA plate was altered (hydrophilized).

Agent Carrying Step

The agent was carried on the surface of the PMMA plate that has been subjected to the hydrophilization treatment step to produce a resin plate carrying the agent. Specifically, 1.1 equivalents of 1-(3-dimethylaminopropyl)-3-ethylcarbodiimide hydrochloride (EDC) and triethylamine were added to 5 ml of 10 mM levofloxacin (agent) aqueous solution as an activator, and the PMMA plate that has been subjected to the hydrophilization treatment step was immersed and allowed to stand at room temperature, and reaction was carried out for 4 hours. In this manner, levofloxacin was carried on the surface of the PMMA plate by an ester bond (covalent bond). In the manner as described above, the agent carrying step was performed. Thereafter, the PMMA plate carrying the agent was further immersed in purified water for 10 minutes to remove excess agent and the like.

Sustained Release of Agent

Figure 11B:
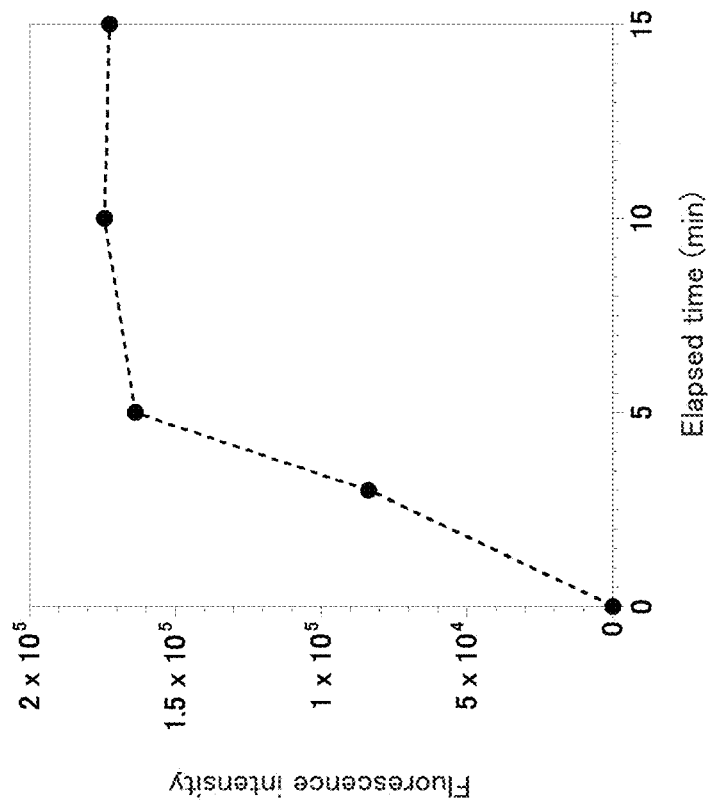
FIGS. 11A and 11B are graphs showing the fluorescence spectrum of PBS in Reference Example B17.
Figure 11A:
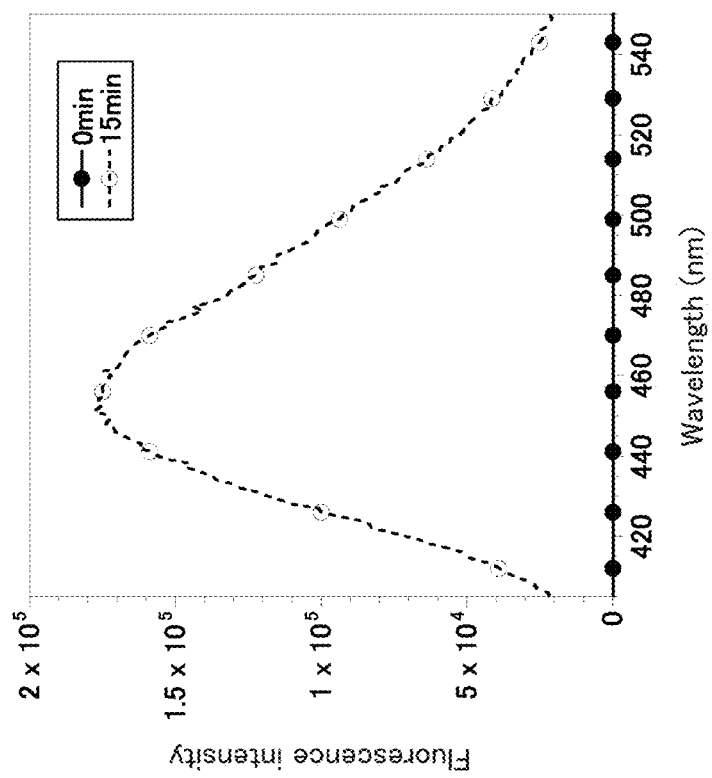

A PMMA plate (acrylic resin base) carrying levofloxacin by the agent carrying step was immersed in phosphate buffered saline (PBS, serum concentration: 10%) in which fetal bovine serum was dissolved for a predetermined time and then taken out. Thereafter, the fluorescence spectrum of levofloxacin liberated in the PBS was measured. In this manner, the time course of sustained-release of levofloxacin from the PMMA plate was verified. The graphs of FIGS. 11A and 11B show the measurement results of the fluorescence spectrum. FIG. 11A is a graph showing the fluorescent spectrum of the PBS at immersion times of 0 minutes (prior to immersion) and 15 minutes. In the graph of FIG. 11A, the horizontal axis indicates the wavelength (nm) and the vertical axis indicates the relative value of the fluorescence intensity. In the graph of FIG. 11B, the horizontal axis indicates the immersion time (elapsed time, min) of the PMMA plate in the PBS, and the vertical axis indicates the relative value of the fluorescent intensity at a wavelength of 450 nm. As shown in FIGS. 11A and 11B, it was verified that levofloxacin was sustain-released over time from the PMMA plate carrying levofloxacin. It is presumed that the ester bond between levofloxacin and the surface of the PMMA plate reacted with the enzyme in the serum to be cleaved, and levofloxacin was sustain-released from the surface of the PMMA plate. Further, as can be seen from FIGS. 11A and 11B, in the present reference example, during the immersion time of 15 minutes in the PBS containing serum, the sustained-release of levofloxacin was almost completed.

Reference Example B18

Figure 12A:
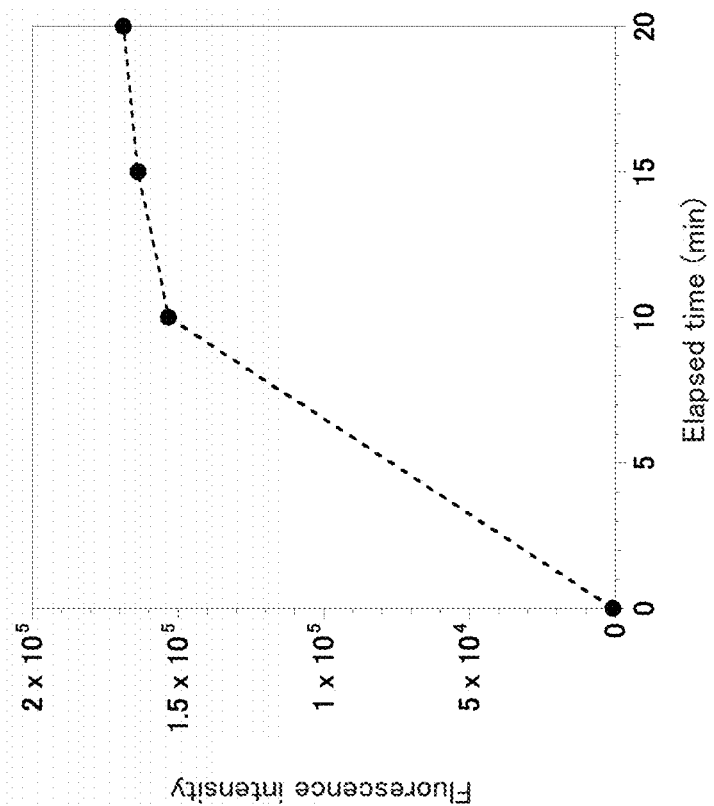
FIGS. 12A and 12B are graphs showing the fluorescence spectrum of PBS in Reference Example B18.
Figure 12B:
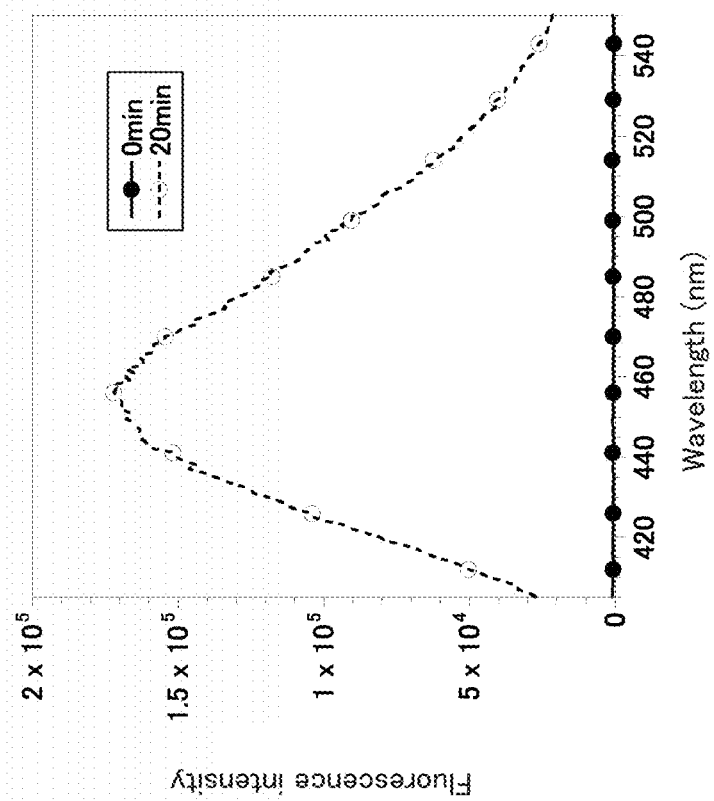

Carrying and sustained-release of the agent were examined in the same manner as in Reference Example B17 except that levofloxacin was carried on the surface of the PMMA plate by ionic bond instead of a covalent bond and that the PBS containing no serum was used instead of the PBS containing serum.
Hydrophilization Treatment Step
The surface of the PMMA plate was altered (hydrophilized) in the same manner as in Reference Example B17 using the same PMMA plate as in Reference Example B17 by the same method as in Reference Example B17.
Agent Carrying Step
The agent was carried on the surface of the PMMA plate that has been subjected to the hydrophilization treatment step to produce a resin plate carrying the agent. Specifically, the agent carrying step was performed by immersing the PMMA plate that has been subjected to the hydrophilization treatment step in a 10 mM levofloxacin (agent) aqueous solution at room temperature and allowing to stand for 4 hours. Thereafter, the PMMA plate was further immersed in purified water for 10 minutes to remove excess agent and the like. On the surface of this PMMA plate, levofloxacin (agent) was carried by an ionic bond.
Sustained Release of Agent
A PMMA plate (acrylic resin base) carrying levofloxacin by the agent carrying step was immersed in PBS (phosphate buffered saline) containing no serum for a predetermined time and then taken out. Thereafter, the fluorescence spectrum of levofloxacin liberated in the PBS was measured. In this manner, the time course of sustained-release of levofloxacin from the PMMA plate was examined. The graphs of FIGS. 12A and 12B show the measurement results of the fluorescence spectrum. FIG. 12A is a graph showing the fluorescent spectrum of the PBS at immersion times 0 minutes (prior to immersion) and 20 minutes of the PMMA plate. In the graph of FIG. 12A, the horizontal axis indicates the wavelength (nm) and the vertical axis indicates the relative value of the fluorescence intensity. In the graph of FIG. 12B, the horizontal axis indicates the immersion time (elapsed time, min) of the PMMA plate in the PBS and the vertical axis indicates the relative value of the fluorescent intensity at a wavelength of 450 nm. As shown in FIGS. 12A and 12B, it was observed that levofloxacin was sustain-released over time from the PMMA plate carrying levofloxacin. Further, as can be seen from FIGS. 12A and 12B, in the present reference example, during the immersion time of 20 minutes in the PBS, the sustained-release of levofloxacin was almost completed.

As shown in Reference Examples B17 and B18, the agent could be carried on the surface of the PMMA plate that has been subjected to hydrophilization treatment both by a covalent bond and an ionic bond. In addition, in both cases, the carried agent could be sustain-released in PBS with or without serum.

An acrylic resin such as PMMA is a main material of a lens to be fitted to an eye (e.g., intraocular lens and contact lens). Therefore, based on Reference Examples B17 and B18, it is presumed that it is possible to sustain-release an agent to a living body from a lens to be fitted to an eye (e.g., an intraocular lens or a contact lens) carrying an agent according to the present invention. While levofloxacin was used in Reference Examples B17 and B18 as the agent, the present invention is not limited thereto, and any agent can be used.

While the present invention has been described above with reference to exemplary embodiments and examples, the present invention is by no means limited thereto. Various changes and alterations that may become apparent to those skilled in the art may be made in the configuration and specifics of the present invention without departing from the scope of the present invention.

INDUSTRIAL APPLICABILITY

As described above, the present invention can provide a new method for producing a lens to be fitted to an eye in a simple manner at a low cost and a lens to be fitted to an eye which can be produced in a simple manner at a low cost. Further, since the lens to be fitted to an eye of the present invention can have various excellent effects as described above, for example, its industrial use value is large.

The present application claims priority from Japanese Patent Application No. 2018-117454 filed on Jun. 20, 2018, the entire disclosure of which is incorporated herein by reference.

REFERENCE SIGNS LIST

1: organic phase (organic phase or fluorous phase)
2: aqueous layer (aqueous phase)
3: gas phase
4: reaction container
5: plate
11: polymer lens
12: altered surface (altered surface of polymer lens 11)
13: agent
101: acidic hydrochloric acid ($NaClO_2$) aqueous solution
102, 104: reaction container
103: lid
105: passage
106: air
107: $ClO_2$ gas
111: polymer

The invention claimed is:
1. A lens to be fitted to an eye, formed of a polymer, wherein
a surface of the polymer is an oxidized surface, the oxidized surface being a hydrophilized surface, wherein the oxidized surface has been hydrophilized by reaction with a chlorine dioxide radical, and a variation X of a contact angle with water represented by the following equation (1) is larger than 0°:

$$X = A_0 - A \quad (1)$$

$A_0$: a contact angle with water on a non-oxidized surface of the polymer

A: a contact angle with water on an oxidized surface of the polymer

X: a variation of the contact angle with water.

2. The lens to be fitted to an eye according to claim 1, wherein the polymer is polypropylene, and in an infrared absorption spectrum of the oxidized surface, a ratio C=O/C—H of an area of a peak derived from C—H expansion and contraction in 2800 to 3000 $cm^{-1}$ to an area of a peak derived from C=O expansion and contraction in 1700 to 1800 $cm^{-1}$ satisfies the following condition:

C=O/C—H>0.

3. The lens to be fitted to an eye according to claim 1, wherein an agent is carried on the surface of the polymer.

4. A lens to be fitted to an eye, formed of a polymer, wherein a surface of the polymer has been hydrophilized by reaction with a chlorine dioxide radical, and an agent is carried on the surface of the polymer which has been hydrophilized.

5. The lens to be fitted to eye according to claim 1, wherein the oxidized surface includes at least one hydrophilic group selected from the group consisting of a hydroxymethyl group (—$CH_2OH$), a formyl group (—CHO), and a carboxyl group (—COOH).

* * * * *